(12) United States Patent
Tötterman et al.

(10) Patent No.: US 8,685,640 B2
(45) Date of Patent: Apr. 1, 2014

(54) MEDICAL METHODS AND AGENTS FOR USE THEREIN

(75) Inventors: Thomas Tötterman, Uppsala (SE); Linda Sandin, Uppsala (SE); Angelica Loskog, Uppsala (SE); Sara Mangsbo, Uppsala (SE); Peter Ellmark, Lund (SE)

(73) Assignee: Alligator Bioscience AB, Lund (SE)

( * ) Notice: Subject to any disclaimer, the term of this patent is extended or adjusted under 35 U.S.C. 154(b) by 0 days.

(21) Appl. No.: 13/510,565

(22) PCT Filed: Nov. 17, 2010

(86) PCT No.: PCT/GB2010/002115
§ 371 (c)(1),
(2), (4) Date: Sep. 5, 2012

(87) PCT Pub. No.: WO2011/061487
PCT Pub. Date: May 26, 2011

(65) Prior Publication Data
US 2013/0004483 A1 Jan. 3, 2013

(30) Foreign Application Priority Data
Nov. 19, 2009 (GB) .................................. 0920258.1

(51) Int. Cl.
*C12Q 1/00* (2006.01)
*G01N 33/53* (2006.01)

(52) U.S. Cl.
USPC .................................................. 435/4; 514/1

(58) Field of Classification Search
None
See application file for complete search history.

(56) References Cited

U.S. PATENT DOCUMENTS 4,816,567 A 3/1989 Cabilly et al.

FOREIGN PATENT DOCUMENTS

| WO | WO-02/48351 A2 | 6/2002 |
| WO | WO-02/48351 A3 | 6/2002 |
| WO | WO-03/097834 A2 | 11/2003 |
| WO | WO-03/097834 A3 | 11/2003 |

OTHER PUBLICATIONS

Simmons et al (Cancer Immunol Immunother, 2008, 57: 1263-1270).*
Curtin et al (PLoS One, 2008, 3(4): 1-17).*
Akagi, T. et al. (2007, e-pub. Apr. 20, 2007). Protein Direct Delivery to Dendritic Cells Using Nanoparticles Based on Amphiphilic Poly(Amino Acid) Derivatives, *Biomaterials* 28:3427-3436.
Berinstein, N.L. (2007). "Enhancing Cancer Vaccines With Immunomodulators," *Vaccine* 25(Suppl. 2):B72-B88.
Boerner, P. et al. (Jul. 1, 1991). "Production of Antigen-Specific Human Monoclonal Antibodies From in Vitro-Primed Human Splenocytes," *J. Immunol.* 147(1):86-95.
Cole, S.P.C. et al. (1984). "Human Monoclonal Antibodies," *Mol. Cell. Bioi.* 62:109-120.
Cole, S.P.C. et al. (1985). "The EBV-Hybridoma Technique and Its Application to Human Lung Cancer," in *Monoclonal antibodies and Cancer Therapy*, Alan R. Liss, Inc., New York, New York, pp. 77-96.
Cote, R.J. et al. (Apr. 1983). "Generation of Human Monoclonal Antibodies Reactive With Cellular Antigens," *Proc. Natl. Acad. Sci. USA* 80:2026-2030.
Davis, S.J. et al. (Mar. 2003). "The Nature of Molecular Recognition by T Cells," *Nat. Immunol.* 4(3):217-224.
De Groot, C.J. et al. (2002). "Therapeutic Efficacy of IL-2-Loaded Hydrogels in a Mouse Tumor Model," *Int. J. Cancer* 98:134-140.
Den Otter, W. et al. (2008, e-pub. Feb. 7, 2008). "Local Therapy of Cancer With Free IL-2," *Cancer Immunol. Immunother.* 57:931-950.
Hodi, F.S. et al. (Aug. 19, 2010). "Improved Survival With Ipilimumab in Patients With Metastatic Melanoma," *N. Engl. J Med* 363(8):711-723.
Hoogenboom, H.R. et al. (1992). "By-Passing Immunisation. Human Antibodies From Synthetic Repertoires of Germline $V_H$ Gene Segments Rearranged in Vitro," *J. Mol. Biol.* 227:381-388.
Jackaman, C. et al. (2008, e-pub. Sep. 29, 2008). "Deliberately Provoking Local Inflammation Drives Tumors to Become Their Own Protective Vaccine Site," *International immunology* 20(11):1467-1479.
Johnson, E.E. et al. (Dec. 2008, e-pub. Dec. 1, 2008). "Intratumoral Immunocytokine Treatment Results in Enhanced Antitumour Effects," *Cancer Immunollmmunother.* 57(12):1891-1902.
Jones P.T. et al. (May 29, 2006). "Replacing the Complementarity-Determining Regions in a Human Antibody With Those From a Mouse," *Nature* 321:522-525.
Kavanagh, B. et al. (Aug. 15, 2008, e-pub. Jun. 3, 2008). "CTLA4 Blockade Expands FoxP3+ Regulatory and Activated Effector CD4+ T Cells in a Dose-Dependent Fashion," *Blood* 112(4):1175-1183.
Khawli, L.A. et al. (2008). "Cytokine, Chemokine, and Co-Stimulatory Fusion Proteins for the Immunotherapy of Solid Tumors," *Handb. Exp. Pharmacal.* 181:291-328.
Köhler, G. et al. (Aug. 7, 1975). "Continuous Cultures of Fused Cells Secreting Antibody of Predefined Specificity," *Nature* 256:495-497.
Kozbor, D. et al. (1985). "Specific Immunoglobulin Production and Enhanced Tumorigenicitiy Following Ascites Growth of Human Hybridomas," *J. Immunol. Methods* 81:31-42.
Kwon, E.D. et al. (Jul. 1997). "Manipulation of T Cell Costimulatory and Inhibitory Signals for Immunotherapy of Prostate Cancer," *Proc. Natl. Acad. Sci. U. S. A.* 94:8099-8103.
Lee, K.M. et al. (Dec. 18, 1998). "Molecular Basis of T Cell Inactivation by CTLA-4," *Science* 282:2263-2266.

(Continued)

*Primary Examiner* — Sean Aeder
(74) *Attorney, Agent, or Firm* — Morrison & Foerster LLP

(57) ABSTRACT

The present invention provides an immunomodulatory agent for use in the local treatment of tumors, wherein the treatment comprises patient-specific optimization of the dose of the immunomodulatory agent to identify the maximum therapeutic dose that does not induce an increase in the number of local regulatory T cells (Treg cells) in the patient The invention further provides methods for the local treatment of tumors as well as methods for optimising treatments for the same.

14 Claims, 14 Drawing Sheets

(56) References Cited

OTHER PUBLICATIONS

Figure 1:
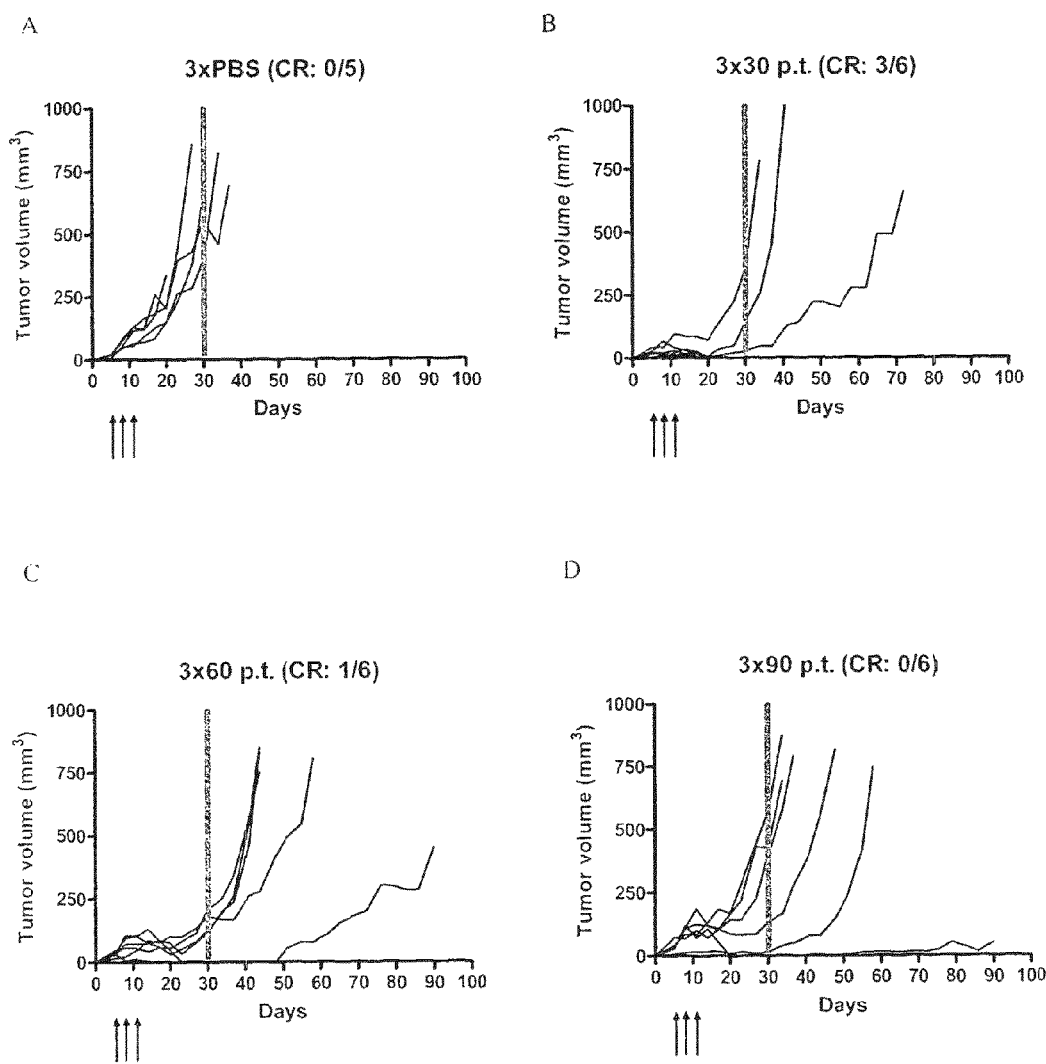

Loskog, A.S. et al. (Dec. 15, 2005, e-pub. Dec. 16, 2005). "AdCD40L Gene Therapy Counteracts T Regulatory Cells and Cures Aggressive Tumors in an Orthotopic Bladder Cancer Model," *Clin. Cancer Res.* 11(24):8816-8821.

Mangsbo, S.M. et al. (Apr. 2010). "Enhanced Tumor Eradication by Combining CTLA-4 or PD-1 Blockade With CpG Therapy," *J. Immunother.* 33(3):225-235.

Marks, J.D. et al. (1991). "By-Passing Immunization Human Antibodies From V-Gene Libraries Displayed on Phage," *J. Mol. Bioi.* 222:581-597.

Melero, I. et al. (Feb. 2007). "Immunostimulatory Monoclonal Antibodies for Cancer Therapy," *Nat. Rev. Cancer.* 7:95-106.

Melero, I. et al. (Mar. 1, 2009). "Palettes of Vaccines and Immunostimulatory Monoclonal Antibodies for Combination," *Clin. Cancer Res.* 15(5):1507-1509.

Melief, C.J.M. (Sep. 19, 2008). "Cancer Immunotherapy by Dendritic Cells," *Immunity* 29:372-383.

Mellor, A.L. et al. (Jan. 2008). "Creating Immune Privilege: Active Local Suppression That Benefits Friends, but Protects Foes," *Nat. Rev. Immunol.* 8:74-80.

O'Day, S.J. et al. (Dec. 15, 2007, e-pub. Nov. 14, 2007). "Targeting Cytotoxic T-Lymphocyte antigen-4 (CTLA-4): A Novel Strategy for the Treatment of Melanoma and Other Malignancies," *Cancer* 110(12):2614-2627.

Orlandi, R. et al. (May 1989). Cloning Immunoglobulin Variable Domains for Expression by the Polymerase Chain Reaction, *Proc. Natl. Acad. Sci. U.S.A.* 86:3833-3837.

Presta L. (1992). "Antibody Engineering," *Curr. Op. Struct. Bioi.* 2:593-596.

Ribas, A. et al. (2007). "Tremelimumab (CP-675,206), A Cytotoxic T Lymphocyte Associated Antigen 4 Blocking Monoclonal Antibody in Clinical Development for Patients With Cancer," *Oncologist* 12:873-883.

Ribas, A. (2008). "Overcoming Immunologic Tolerance to Melanoma: Targeting CTLA-4 With Tremelimumab (CP-675,206)," *Oncologist* 13(Suppl 4):10-15.

Riechmann L. et al. (Mar. 24, 1988). "Reshaping Human Antibodies for Therapy," *Nature* 332:323-327.

Sandin, L.C, et al.(Sep. 16, 2010). "In situ CTLA-4 Blockade Mediates Regression of Local and Distant Tumors With Minimal Side Effects," ISBTs Washington, D.C., 1 page.

Sandin, L.C. et al. (Oct. 2011). "Peritumoral CD40 Antibody Delivery: Improved LN Uptake and Superior Anti-Tumor Response," Annual Immunotherapy Symposium, New York, New York, 1 page.

Shaker, M.A. et al. (2009). "Interleukin-2: Evaluation of Routes of Administration and Current Delivery Systems in Cancer Therapy," *J. Pharm. Sci.* 98(7):2268-2298, pp. 1-31.

Stagg, J. et al. (2007). "From Cancer Immunosurveillance to Cancer Immunotherapy," *Immunol. Rev.* 220:82-101.

Totterman, T.H.et al. (2005). The Immunotherapy of Prostate and Bladder Cancer, *BJU Int.* 96:728-735.

Van Herpen, C.M. et al. (Aug. 1, 2003, e-pub. Aug. 11, 2003). "Pharmacokinetics and Immunological Aspects of a Phase lb Study With Intratumoral Administration of Recombinant Human Interleukin-12 in Patients With Head and Neck Squamous Cell Carcinoma: A Decrease of T-Bet in Peripheral Blood Mononuclear Cells," *Clin. Cancer Res.* 9:2950-2956.

Van Herpen, C.M.L. et al. (2008, e-pub. Aug. 26, 2008). "Intratumoral rhll-12 Administration in Head and Neck Squamous Cell Carcinoma Patients Induces B Cell Activation," *Int. J. Cancer* 123:2354-2361.

Van Horssen, R. et al. (2006). "TNF-α in Cancer Treatment: Molecular Insights, Antitumour Effects, and Clinical Utility," *Oncologist* 11:397-408.

Van Mierlo, G.J.D. et al. (Apr. 16, 2002). "CD40 Stimulation Leads to Effective Therapy of CD40 Tumours Through induction of Strong Systemic Cytotoxic T Lymphocyte Immunity," *Proc. Natl. Acad. Sci. U.S.A.* 99(8):5561-5566.

Van Mierlo, G.J.D. et al. (2004). "Activation of Dendritic Cells That Cross-Present Tumor-Derived Antigen Licenses CDS$^+$ CTL to Cause Tumour Eradication," *J. Immunol.* 173:6753-6759.

Verhoeyen, M. et al. (Mar. 25, 1988). "Reshaping Human Antibodies: Grafting an Antilysozyme Activity," *Science* 239(4847):1534-1536.

Von Euler, H. et al. (May 2008). "Efficient Adenovector CD40 Ligand Immunotherapy of Canine Malignant Melanoma," *J. Immunother.* 31(4):377-384, eight pages.

Waldmann, T.A. (2006, e-pub. Sep. 21, 2005). "Effective Cancer Therapy Through immunomodulation," *Annu. Rev. Med.* 57:65-81.

Weber, J. (2007). "Review: Anti-CTLA-4 Antibody Ipilimumab: Case Studies of Clinical Response and Immune-Related Adverse Events," *Oncologist* 12:864-872.

Weber, J.S. et al. (Dec. 20, 2008, e-pub. Nov. 17, 2008). "Phase I/II Study of Ipilimumab for Patients With Metastatic Melanoma," *J. Clin. Oncol.* 27(36):5950-5956.

Winter, G. et al. (Jan. 24, 1991). "Man-Made Antibodies," *Nature* 349:293-299.

Wolchok, J.D. et al. (2009, e-pub. Nov. 24, 2009). "Guidelines for the Evaluation of Immune Therapy Activity in Solid Tumors: Immune-Related Response Criteria," *Clin. Cancer Res.* 15(23):7412-7420.

Yang, J.C. et al. (2007, e-pub. Decmeber 12, 2007). "Ipilimumab (Anti-CTLA4 Antibody) Causes Regression of Metastatic Renal Cell Cancer Associated With Enteritis and Hypophysitis," *J. Immunother.* 30(8):825-830.

Zhang, T. et al. (Apr. 2009, e-pub. Oct. 16, 2009). "Combination of Active Specific Immunotherapy or Adoptive Antibody or Lymphocyte Immunotherapy With Chemotherapy in the Treatment of Cancer," *Cancer Immunollmmunother.* 58:475-492.

International Search Report mailed on Feb. 22, 2011, for PCT Application No. PCT/GB2010/002115, filed on Nov. 17, 2010, two pages.

Liakou, C.I. et al. (Sep. 2008). "CTLA-4 Blockade Increases IFN Gamma-Producing CD4$^+$ ICOS$^{hi}$ Cells to Shift the Ratio of Effector to Regulatory T Cells in Cancer Patients," *PNAS USA* 105(39):14987-14992.

Quezada, S. et al. (Jul. 3, 2006). "CTLA4 Blockade and GM-CSF Combination Immunotherapy Alters the Intratumor Balance of Effector and Regulatory T Cells," *Journal of Clinical Investigation* 116(7):1935-1945.

Simmons, A.D. et al. (Jan. 31, 2008). "Local Secretion of Anti—CTLA-4 Enhances the Therapeutic Efficacy of a Cancer Immunotherapy With Reduced Evidence of Systemic Autoimmunity," *Cancer Immunology Immunother.* 57(8):1263-1270.

Tuve, S. et al. (Jun. 2007). "Combination of Tumor Site-Located CTL-Associated Antigen-4 Blockade and Systemic Regulatory T-Cell Depletion Induces Tumor-Destructive Immune Responses," *Cancer Research* 67(12):5929-5939.

Written Opinion mailed on Feb. 22, 2011, for PCT Application No. PCT/GB2010/002115, filed on Nov. 17, 2010, six pages.

\* cited by examiner

FIGURE 2
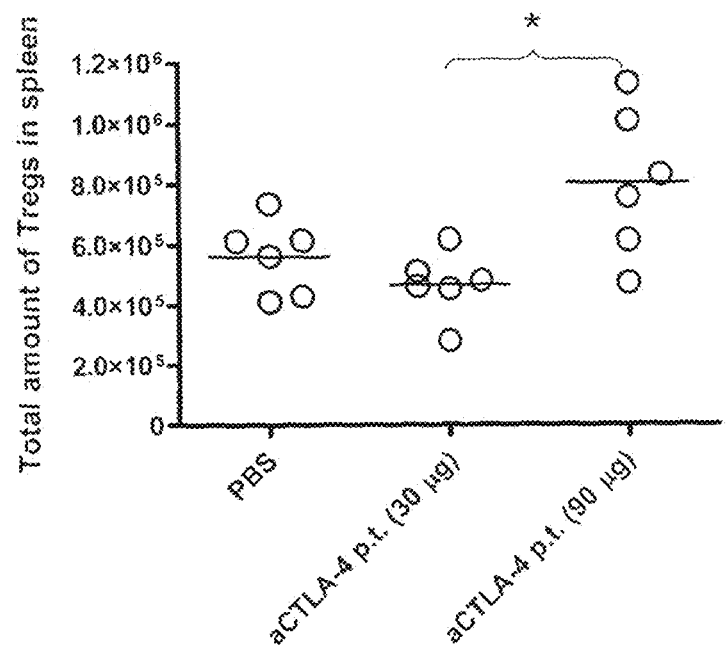
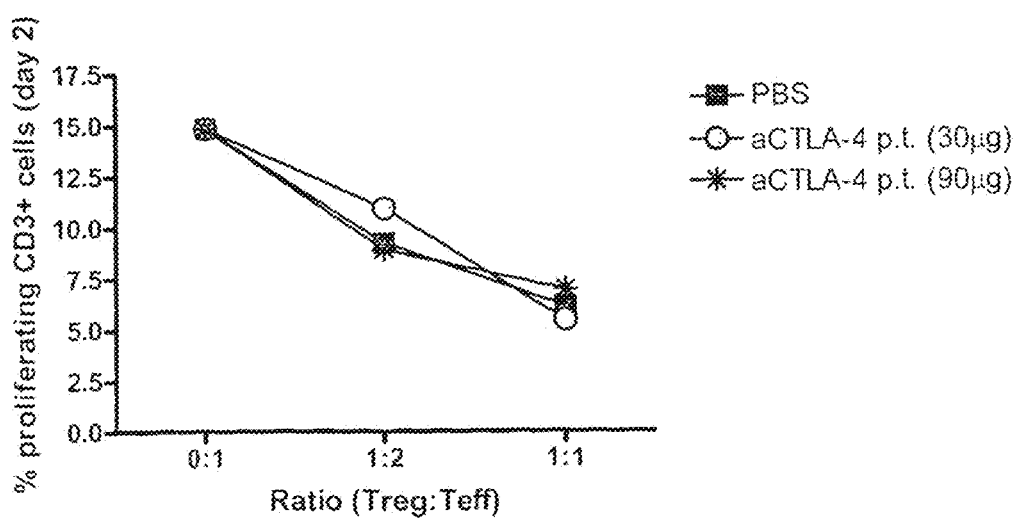

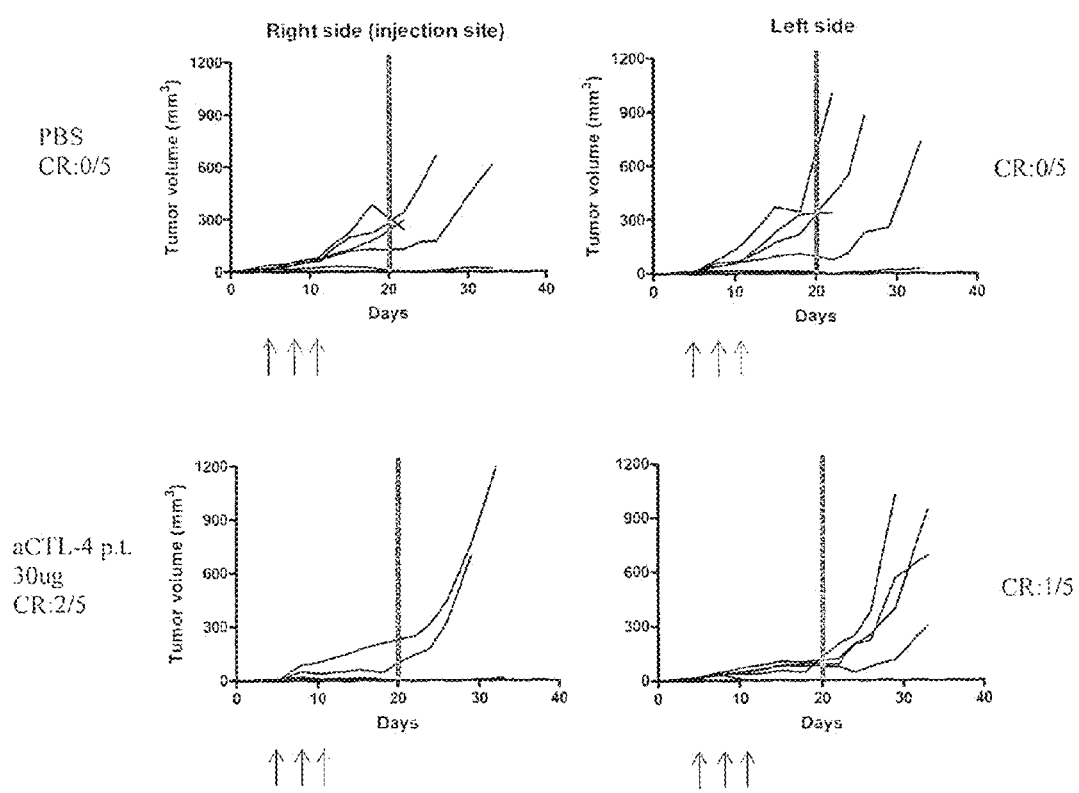

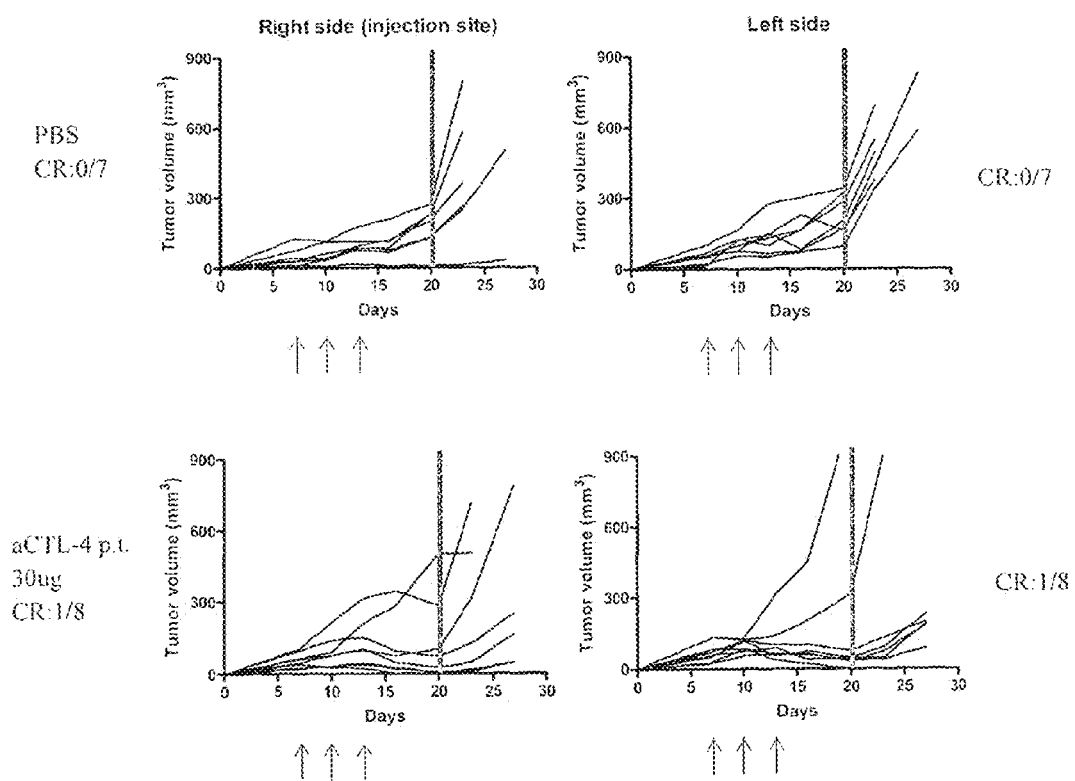

Figure 5:
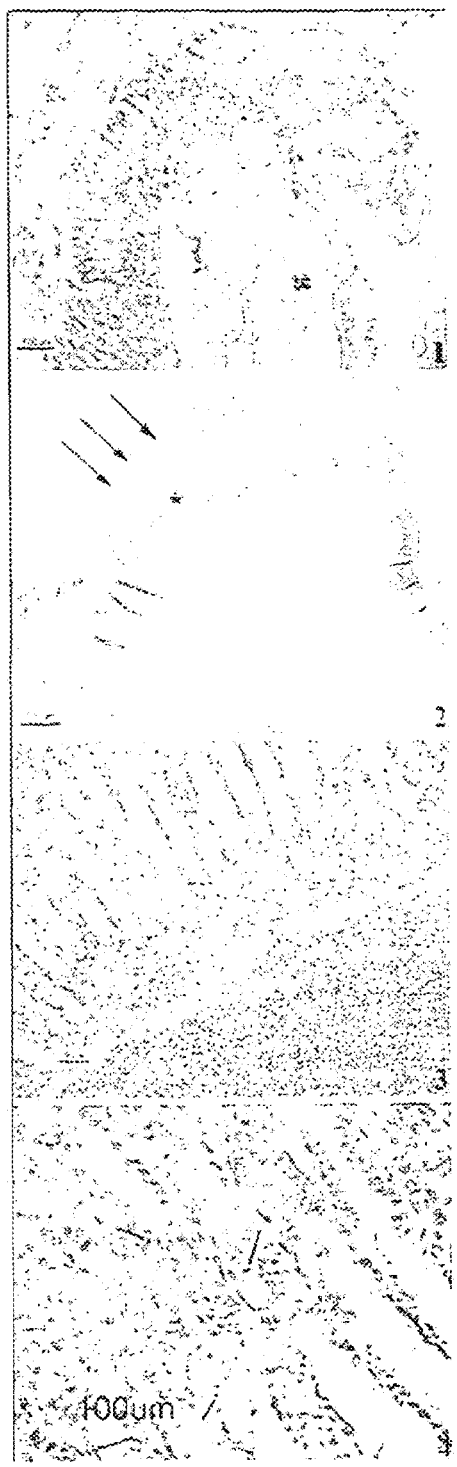

FIGURE 5
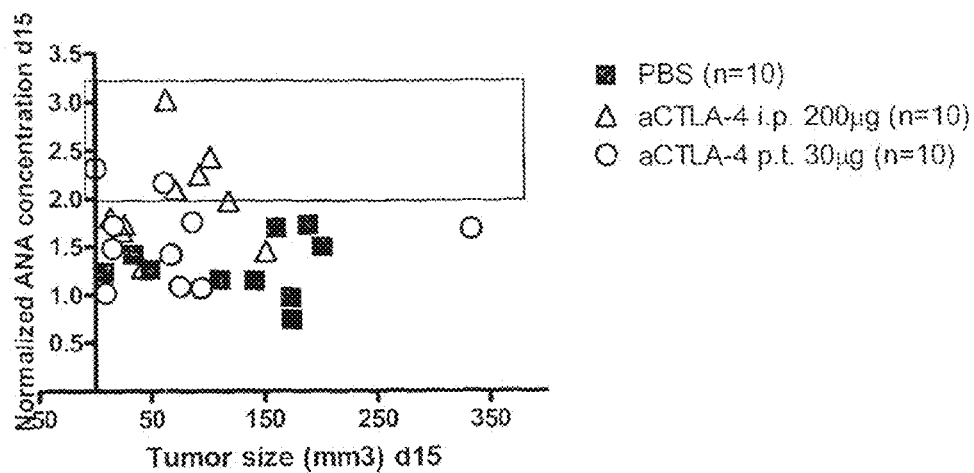
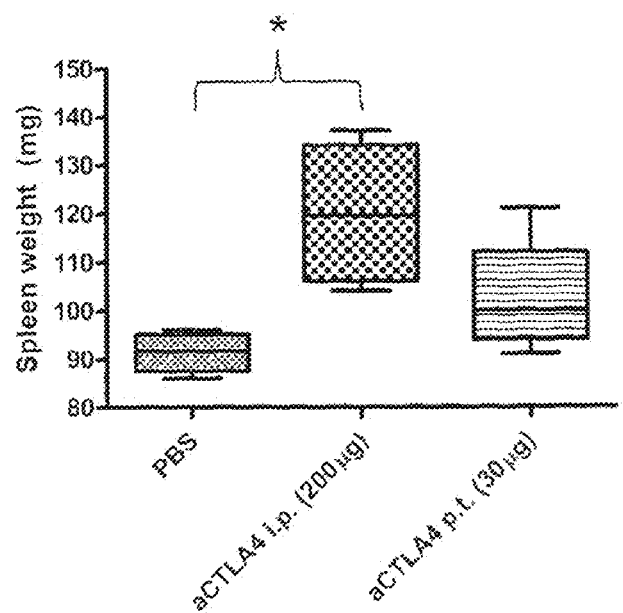

C

FIGURE 6
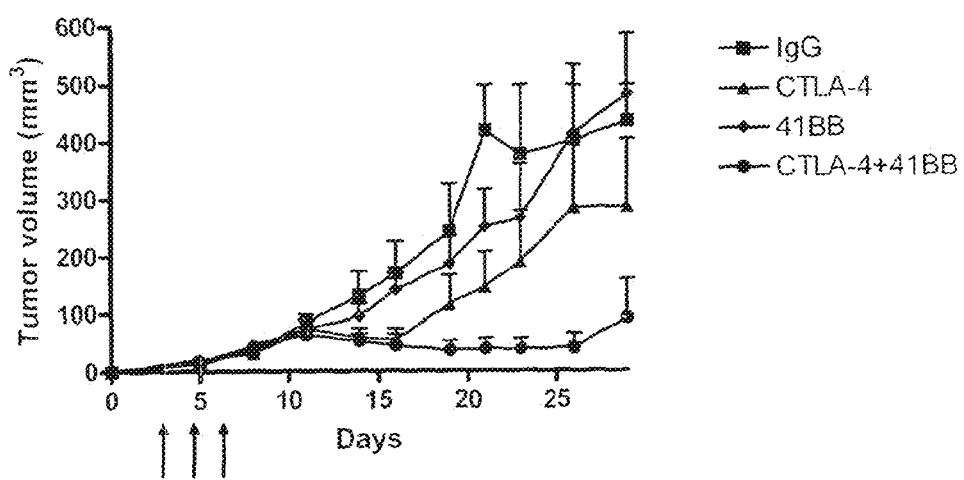
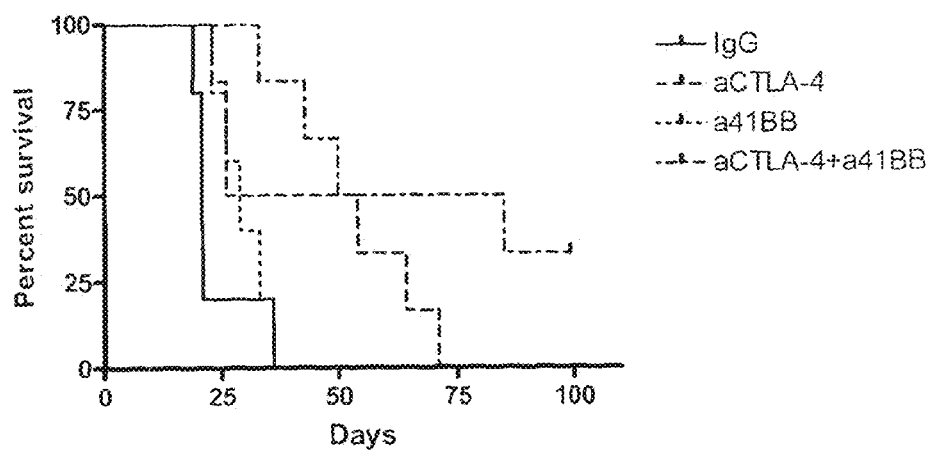

FIGURE 7
A
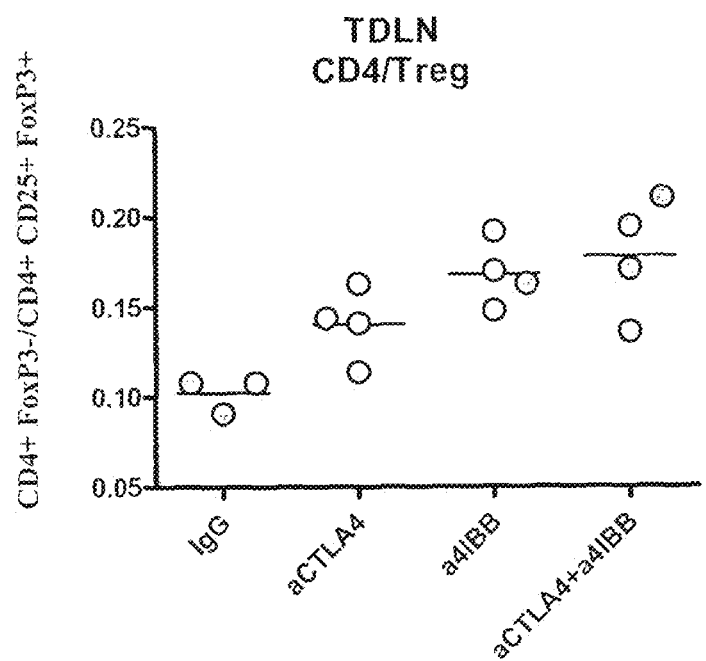
B
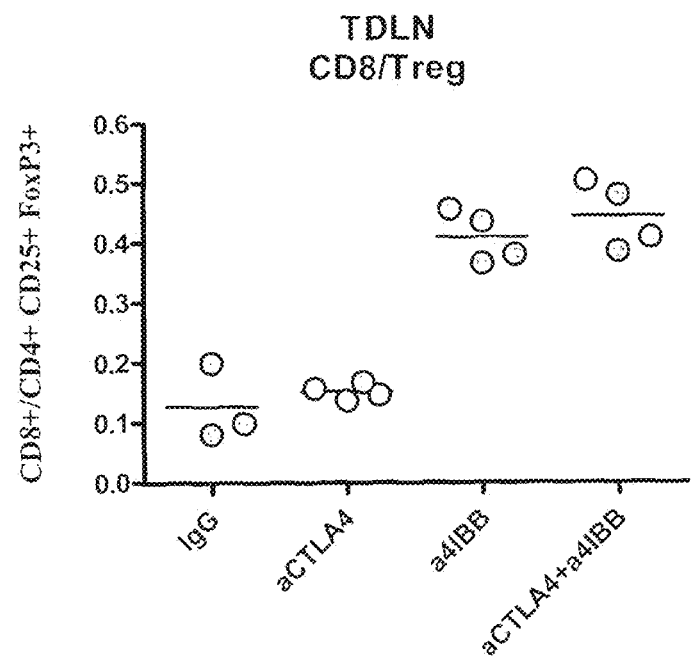

FIGURE 7 (continued)
C
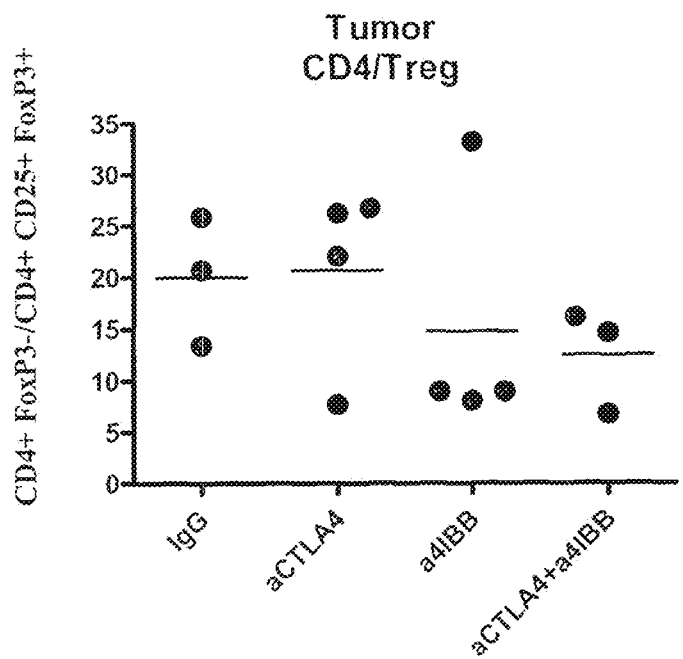
D
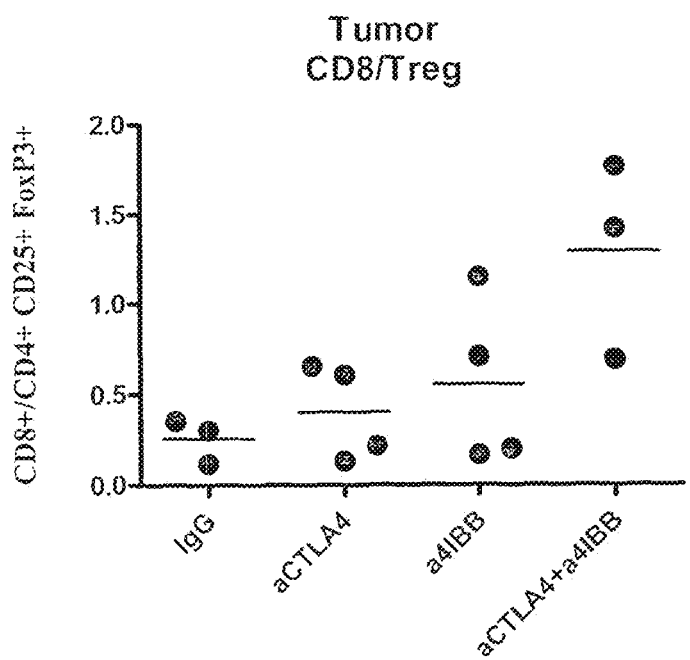

Figure 8:
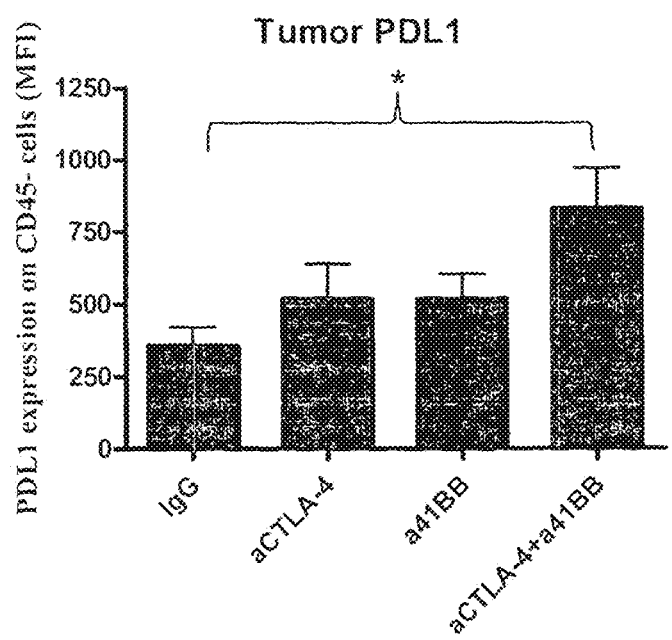

FIGURE 8
A
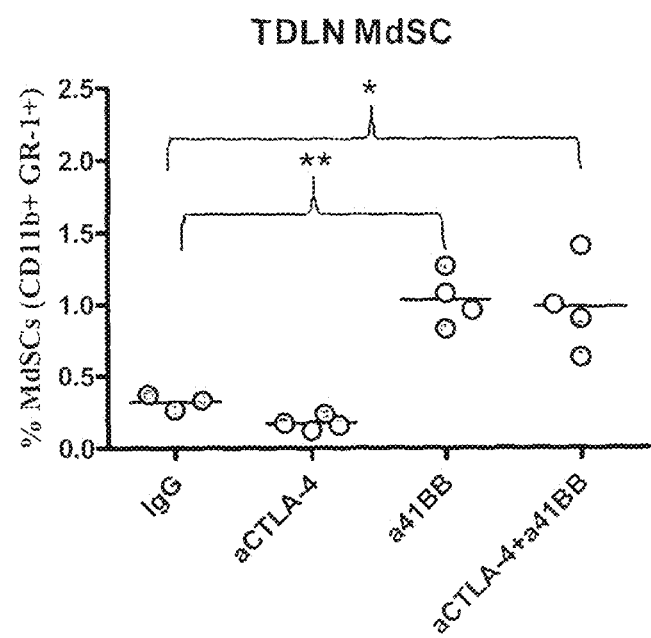
B
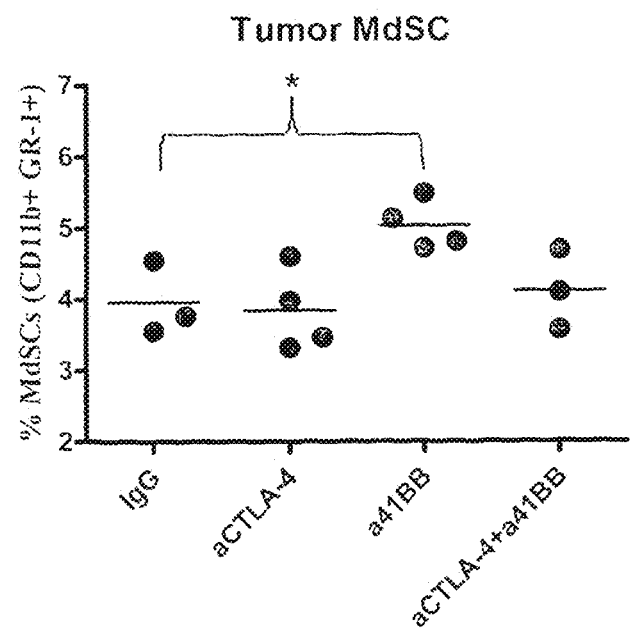

MEDICAL METHODS AND AGENTS FOR USE THEREIN

CROSS-REFERENCE TO RELATED APPLICATIONS

This application is a National Phase application under 35 U.S.C. §371 of International Application No. PCT/GB2010/002115 filed Nov. 17, 2010 and claims the benefit of Great Britain Application No. 0920258.1 filed Nov. 19, 2009, the disclosures of which are incorporated herein by reference in their entirety.

FIELD OF INVENTION

The present invention relates to dose-optimised methods of local tumour immunotherapy and agents for use in the same. In particular, there is provided a method of local administration of immunomodulatory agents in the treatment of tumours comprising patient-specific optimisation of the dose of a CTLA-4 blocking agent to identify the maximum therapeutic dose that does not induce an increase in the number of local regulatory T cells in the patient.

INTRODUCTION

Cancer accounts for over 30% of deaths in the developed countries. Whereas great progress has been achieved in the treatment of certain tumours (Hodgkin's disease, some lymphomas/leukaemias, localized cutaneous cancer), conventional therapies such as surgery, chemotherapy, and radiotherapy are ineffective in curing disseminated solid tumours. Immunotherapy (synonymous with biological therapy) of cancer holds great promise for treatment of several different types of cancer, also disseminated, metastatic tumours (Stagg et al., 2007, *Immunol Rev.* 220:82-101, Melief, 2008, *Immunity.* 29:372-383, Melero et al., 2007, *Nat Rev Cancer.* 7:95-106, Waldmann, 2006, *Annu. Rev Med.* 57:65-81, Khawli et al., 2008, *Handb. Exp. Pharmacol.* 181:291-328, Berinstein, 2007, *Vaccine.* 25 Suppl 2: B72-B88, Mellor. & Munn, 2008, *Nat Rev Immunol.* 8:74-80). It aims at activating the patient's immune system to fight the cancer and generate a long term eradication of the tumour cells.

The different approaches to cancer immunotherapy include the following:

1) Monoclonal antibody (Mab) therapy can be used to i) target cancer cells (e.g. Rituximab) for destruction, either using the antibodies naked or conjugated to a toxin, ii) to block growth factor receptors (Herceptin) or iii) to stimulate the immune system.

2) Cancer vaccines includes tumour cell vaccines (autologous or allogeneic), antigenic vaccines and dendritic cells vaccines, DNA vaccines, and vector based vaccines (e.g. adenovirus based gene transfer).

3) Non-specific immunotherapies and adjuvants acts by stimulating the immune system more generally and thereby activating tumour specific immune cells that have been suppressed by the tumour environment. This could be done either by stimulating or activating immune effector cells giving an immune reaction to the tumour (e.g. effector T cells, or $T_{eff}$ cells) or by inhibiting or inactivate cells with an inhibitory phenotype (e.g. regulatory T cells, or $T_{reg}$ cells). An approach like this will include active molecules like cytokines, bacterial adjuvants as well as drugs (including mAbs) that targets immunoregulatory receptors (e.g. CTLA-4 and CD40). Additional approaches includes adoptive T cell transfer and $T_{reg}$ depletion therapies, which falls somewhere between the two latter groups.

Malignant melanoma and renal cell carcinoma have been in focus for immunotherapy because of their inherent immunogenicity and the poor response to conventional treatment. However, immunotherapeutic approaches have the potential to be used in a large number of cancer forms, including pancreas, gastrointestinal and bladder cancer[8]. Bladder cancer is another interesting indication for immunotherapy, it has been treated by immunotherapy (BCG) for many years, and it is relatively easy to compartmentalise the treatment of this disease (Totterman, 2005, *BJU. Int.* 96:728-735).

Current research is focused on how to revert the immunosuppressive tumour micro milieu, using immunotherapeutic strategies aiming at 1) activating professional antigen presenting cells (APC) such as dendritic cells (DC) via e.g. CD40, CD137 or Toll-like receptors (TLR), 2) using cytokines, such as IL-2, IL-12 and interferons to stimulate the lymphocytes, or 3) blocking signals that suppress T cell activation by targeting e.g. Cytotoxic T-Lymphocyte Antigen 4 (CTLA-4) or inhibitory receptor programmed death 1 (PD-1) (Stagg et al., 2007, *Immunol Rev.* 220:82-101, Melief, 2008, *Immunity.* 29:372-383, Melero et al., 2007, *Nat Rev Cancer.* 7:95-106, Waldmann, 2006, *Annu. Rev Med.* 57:65-81, Khawli et al., 2008, *Handb. Exp, Pharmacol.* 181:291-328, Berinstein, 2007, Vaccine. 25 Suppl 2: B72-B88, Mellor. & Munn, 2008, *Nat Rev Immunol.* 8:74-80).

However, systemic Immunotherapy is associated with dose limiting toxic side effects, such as autoimmune reactions (colitis, dermatitis etc) for CTLA-4 blockade, and cytokine release syndrome for CD40 agonists. Although these side effects are manageable, the patients have to be observed for symptoms and may require hospitalisation due to treatment of the side effects. This may increase patient inconvenience, increase treatment cost and limit the efficacy of the treatment. One promising approach to minimize the systemic side effects, while retaining the systemic anti-tumour effects is local immunotherapy.

Local immunotherapy compared to systemic treatment is: 1) safer (less toxic) 2) can be used at lower dose, 3) and will generate a similar or improved anti-tumour response, also systemic, for treatment of disseminated tumours. Clinical studies where local (peritumoral=juxtatumoral, intratumoral, intralesional etc. vs. systemic treatments have been evaluated is mainly based on IL-2 treatment (Melenoma and renal cancer). Systemic IL-2 (15.5 kDa t1/7-14 min (initial phase), respective 85 min (secondary phase) treatment is associated with vascular leakage syndrome, and the therapeutic window is small (Shaker & Younes, 2009, *J Pharm Sci.* 98(7):2268-98). Systemic administration of IL-2 is the approved administration route, however, both pre-clinical and clinical data strongly indicates that a local administration regime is preferable (Shaker &Younes, 2009, *J Pharm Sci.* 98(7):2268-98, Den et al., 2008, *Cancer Immunol Immunother.* 57:931-950). The main reason is that the effective dose is lower when administered locally, and the resulting toxicity is much lower. In fact, the therapeutic effect of IL-2 seems to be higher when administered intratumorally. This is probably due to the induction of IL-2 induced vascular leakage in the tumour resulting in massive tumour necrosis, and there are preclinical data (and one small clinical study) demonstrating that intratumoral is more effective than peritumoral administration. The pre-clinical data supporting generation of systemic, metastasis clearing immunity after IL-treatment is substantial (Shaker &Younes, 2009, *J Pharm Sci.* 98(7):2268-98, Den et al., 2008, *Cancer Immunol Immunother.* 57:931-950, De Groot et al., 2002, *Int. J Cancer* 98:134-140). In addition, local administration may improve access to draining tumour lymph nodes. There are also one clinical study that suggest that systemic metastasis clearing effects can be achieved in humans by local administration (Shaker & Younes, 2009, *J Pharm Sci.* 98(7):2268-98, Den et al., 2008, *Cancer Immunol Immunother.* 57:931-950).

The group of Melief et al (van Mierlo et al., 2002, *Proc. Natl. Acad. Sci. U.S.A.* 99:5561-5566, van Mierlo et al., 2004, *J Immunol* 173:6753-6759) has demonstrated that although systemic anti-CD40 treatment resulted in a potent anti-CD40 effect, it also resulted in side effects (shock syndrome). No side effects were seen when the anti-CD40 antibody was injected intratumorally, yet it resulted in systemic anti-tumour effect comparable to i.v. treated mice (van Mierlo et al., 2002, *Proc. Natl. Acad. Sci. U.S.A.* 99:5561-5566). Mice treated intratumorally in one flank were able to clear tumours in the opposite flank (van Mierlo et al., 2002, *Proc. Natl. Acad. Sci. U.S.A.* 99:5561-5566). This anti-tumour effect depend on DC activation and subsequent activation of a CTL response (van Mierlo, G. J. et al. Activation of dendritic cells that cross-present tumor-derived antigen licenses CD8+ CTL to cause tumor eradication. J Immunol 173, 6753-6759 (2004). These results have been verified by Jackaman et al (Jackaman et al., 2008, *International immunology.* 20, 1467-1479). They studied intratumoural injection of anti-CD40 antibodies alone or in combination with IL-2 in a malignant mesothelioma model (C57BL/6J).

In the well-known two-signal model, T cells require interaction between the TCR and antigen in conjunction with MHC class I but also costimulation provided by interaction of CD28 and CD80/86 to become activated. Cytotoxic T Lymphocyte Antigen-4 (CTLA-4), commonly known for its negative regulatory effect on activated CTLs, plays an important role in the maintenance of peripheral tolerance. Several mechanisms account for the suppressive effects induced by CTLA-4-CD80/86 interaction. The relative levels of CD80/86, the stronger affinity of CTLA-4 with CD80 and CD28 with CD86, the physical block of CD28 entering the immunological synapse as well as an intracellular signaling leading to less IL-2 transcription are all part of the inhibitory properties of CTLA-4 (Davis et al., 2003, *Nat. Immunol.* 4, 217-224, Lee et al., 1998, Science 282, 2263-2266). Blockade of this molecule with monoclonal antibodies has been extensively used for its effective anti-tumour effect in many experimental tumour models (Kwon et al., 1997, *Proc. Natl. Acad. Sci. U.S.A.* 94, 8099-8103, Tuve et al., 2007, *Cancer Res.* 67, 5929-5939, Van Horssen et al., 2006, *Oncologist.* 11, 397-408, van Herpen, C et al., 2008, *Int. J Cancer* 123, 2354-2361, van Herpen et al., 2003, *Clin Cancer Res* 9, 2950-2956, Johnson et al., 2008, *Cancer Immunol Immunother.* 57, 1891-1902). Responses have also been registered in patients suffering from metastatic melanoma and renal, prostate and ovarian cancer. So far systemic CTLA-4 therapy has been associated with autoimmune events like nephritis, colitis, skin rash and thyroditis.

CTLA-4 blockade using anti-CTLA-4 antibodies administered after primary tumour resection reduce metastatic relapse in a murine model system (Kwon et al., 1997, *Proc. Natl. Acad. Sci. U.S.A.* 94, 8099-8103). Furthermore, Tuve et al (Tuve et al., 2007, *Cancer Res.* 67, 5929-5939) has demonstrated that anti-CTLA-4 treatment of TC-1 tumour bearing mice, where the tumour itself expressed the anti-CLA-4 antibody exerted a potent anti-tumour effect without induction of autoimmunity. The mice were also protected against tumour re-challenge. In this model, systemic anti-CTLA antibodies resulted in autoimmunity, but not anti-tumour effect.

TNF-apha treatment clinical trials isolated limb perfusion is another example of a clinically approved treatment where a therapy that has an unacceptable toxicity profile when administered systemically can be safely used for local cancer treatment of sarcoma (approved in Europe) (Van Horssen et al., 2006, *Oncologist.* 11, 397-408, van Herpen, C et al., 2008, *Int. J. Cancer* 123, 2354-2361, van Herpen et al., 2003, *Clin Cancer Res* 9, 2950-2956) have demonstrated that intratumoral IL-12 administration in head and neck squamous cell carcinoma in humans is safe and induce a relevant immunological response.

The advantages with intratumoral injection over intravenous have also been demonstrated by Johnson et al (Johnson et al., 2008, *Cancer Immunol Immunother.* 57, 1891-1902). They studied administration of immunocytokines (tumour targeting antibodies coupled to IL-2). They obtained a more potent effect with less immunocytokine IT compared to IV and was effective also on distal tumours. The anti-tumour effect was systemic and generated a memory response as demonstrated by rejection upon tumour re-challenge.

Clinical data demonstrate that local IL-2 treatment of cancer results in similar or improved efficacy, potentially also metastasis clearing, at a lower dose and is associated lower toxicity. Furthermore, clinical data from studies with AdCD40L indicates that this local approach is safe and does not result in cytokine release syndrome and hepatoxicity.

However, there remains a need for improved tumour therapies.

SUMMARY OF THE INVENTION

A first aspect of the invention provides an immunomodulatory agent capable of inhibiting an activity of cytotoxic T lymphocyte antigen 4 (CTLA-4; also known as CD152, CELIAC3, GSE and IDDM12) for use in the local treatment of a tumour in a patient, wherein the treatment comprises patient-specific optimisation of the dose of the immunomodulatory agent to identify the maximum therapeutic dose that does not induce an increase in the number of local regulatory T cells ($T_{reg}$ cells) in the patient.

By "local" treatment of tumour we mean that the immunomodulatory agent is administered in the vicinity of the tumour, for example directly into the tumour or at the site of the tumour.

In one embodiment, the tumour is solid.

In one embodiment, the tumour is disseminated (i.e. metastatic).

For example, the tumour may be selected from the group consisting of tumours of the pancreas, bladder, skin (e.g. melanomas), kidney, prostate gland, breast, lymph nodes, ovary, lung, brain, head, neck, blood and bone marrow (e.g. leukaemias), and GI tract (stomach, colon, rectum).

In one embodiment, the treatment of tumours comprises injection of the immunomodulatory agent. For example, the injection may be intratumoral, peritumoral, juxtatumoral, intralesional and/or into a tumour draining lymph node.

By "an immunomodulatory agent capable of inhibiting an activity of cytotoxic T lymphocyte antigen 4 (CTLA-4)" we mean agents that are capable of inhibiting, at least in part, CTLA-4-induced inhibition of T cells. In particular, we include agents that are capable of blocking the interaction of CTLA-4 with B7-1 (CD80) and/or B7-2 (CD86) in vivo. For example, the immunomodulatory agent may capable of binding in vivo to CTLA-4, B7-1 and/or B7-2, thereby inhibiting (at least in part) the interaction between these immunomodulatory molecules. Thus, the immunomodulatory agent may inhibit the activity of CTLA-4 by at least 10% compared to its activity in the absence of the immunomodulatory agent, for example by at least 20%, 30%, 40%, 50%, 60%, 70%, 80% or 90%. Advantageously, the immunomodulatory agent inhibits the activity of CTLA-4 completely.

It will be appreciated by persons skilled in the art that any agent capable of inhibiting the activity of CTLA-4 in vivo may be used in the present invention.

Such agents may be identified using methods well known in the art, such as:
(a) by determining the effect of a test agent on levels of expression of CTLA-4 mRNA, for example by Southern blotting or related hybridisation techniques;
(b) by determining the effect of a test agent on levels of CTLA-4 protein, for example by immunoassays using anti-CTLA-4 antibodies; and
(c) by determining the effect of a test agent on a functional marker of CTLA-4 activity, for example its ability to bind B7-1(CD80) and/or B7-2(CD86).

In one embodiment of the invention, the agent is an inhibitor of the expression (i.e. transcription and/or translation) of CTLA-4. Thus, the agent may be a short interfering RNA (siRNA) molecule or an antisense oligonucleotide. For example, the agent may comprise or consist of a short nucleotide sequence (10 to 30 nucleotides) which is complementary to a region of mRNA encoding human CTLA-4 (see GenBank Accession No. L15006.1).

In a further embodiment of the invention, the agent is an inhibitor of the binding properties of CTLA-4. For example, the agent may interfere with the binding of CTLA-4 to an endogenous ligand/receptor, such as B7-1(CD80) and/or B7-2(CD86). This may be achieved by the agent binding to CTLA-4 so as to inhibit or prevent its binding to B7-1(CD80) and/or B7-2(CD86). Alternatively, the agent may bind to B7-1(CD80) and/or B7-2(CD86) so as to inhibit or prevent binding to CTLA-4. Binding of the natural ligands (B7-1 and B7-2) to CTLA-4 induces an immune inhibitory/suppressive effect, thus blockade of their binding inhibits the suppressive event.

In a still further embodiment of the invention, the agent may inhibit the biological activity of CTLA-4 by modulating (for example, reducing) the stability of CTLA-4 or its mRNA.

Advantageously, the agent is capable of inhibiting the biological activity of CTLA-4 selectively.

By 'selectively' we mean that the agent inhibits the biological activity of CTLA-4 to a greater extent than it modulates the activity of other proteins in the cancer cells. Preferably, the agent inhibits only the biological activity of CTLA-4, although it will be appreciated that the expression and activity of other proteins within the cancer cells may change as a downstream consequence of a selective inhibition of CTLA-4. Thus, we exclude agents which have a non-specific effect on gene expression and/or cancer cell growth.

It will be appreciated by persons skilled in the art that inhibition of the biological activity of CTLA-4 by an agent of the invention may be in whole or in part. For example, the agent may inhibit the biological activity of CTLA-4 by at least 10%, preferably at least 20%, 30%, 40%, 50%, 60%, 70%, 80% or 90%, and most preferably by 100% compared to the biological activity of CTLA-4 in cells which have not been exposed to the agent. In a preferred embodiment, the agent is capable of inhibiting the biological activity of CTLA-4 by 50% or more compared to the biological activity of CTLA-4 in cells which have not been exposed to the agent.

Advantageously, the immunomodulatory agent comprises or consists of a polypeptide.

In one embodiment, the immunomodulatory agent is not an antibody or antigen-binding fragment or derivative thereof.

For example, the immunomodulatory agent may be a soluble ligand (such as modified B7-1 or B7-2, engineered natural ligands for CTLA-4; see NCBI Sequence No. NM_005191.3 and GenBank No. U04343.1, respectively). In contrast to cell surface-bound ligands, such soluble ligands do not form receptor/ligand multimer-complexes and so act to inhibit CTLA-4-mediated signalling pathways.

In an alternative embodiment, the immunomodulatory agent comprises or consists of an antibody or antigen-binding fragment or derivative thereof.

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to the same antigen.

Preferably, the antigen-binding fragment is selected from the group consisting of Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]).

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

Also included within the scope of the invention are modified versions of antibodies and antigen-binding fragments thereof, e.g. modified by the covalent attachment of polyethylene glycol or other suitable polymer.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann at al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

Once suitable antibodies are obtained, they may be tested for activity, for example by ELISA.

In one embodiment, the antibody is a monoclonal antibody.

In one embodiment, the antibody or antigen-binding fragment or derivative thereof is human or humanised.

In one embodiment, the antibody or antigen-binding fragment or derivative thereof lacks a functional Fc portion.

In one embodiment, the immunomodulatory agent is capable of binding CTLA-4. For example, the immunomodulatory agent may comprise or consist of an anti-CTLA-4 antibody, or antigen-binding fragment or derivative thereof, with CTLA-4 antagonist activity (e.g. ipilimumab, BMS/Medarex).

In one embodiment, the immunomodulatory agent is non-naturally occurring.

In one embodiment, the immunomodulatory agent is the product, directly or indirectly, of in vitro protein optimisation (e.g. using the FIND® technology of Alligator Bioscience AB, as described in WO 02/48351 and WO 03/097834).

In one embodiment, the immunomodulatory agent of the first aspect of the invention (referred to hereinafter as the "first immunomodulatory agent") is for use in combination with a second active agent.

The second active agent may be a second immunomodulatory agent. For example, the second active agent may be capable of binding in vivo to an immune cell co-receptor.

In one embodiment, the (first) immunomodulatory agent is a direct activator of the immune system and the second immunomodulatory agent is an inhibitor of immune suppressive cells or events, or vice-versa.

In one embodiment, the (first) immunomodulatory agent is a CTLA-4 inhibitor and the second immunomodulatory agent is a cytokine.

For example, the (first) immunomodulatory agent may be an anti-CTLA-4 antibody or antigen-binding fragment or derivative thereof with CTLA-4 antagonist activity and the second immunomodulatory agent may be IL-2.

Alternatively, the (first) immunomodulatory agent is a CTLA-4 inhibitor and the second immunomodulatory agent is a CD40 agonist. For example, the (first) immunomodulatory agent may be an anti-CTLA-4 antibody or antigen-binding fragment or derivative thereof with CTLA-4 antagonist activity and the second immunomodulatory agent may be an anti-CD40 antibody or antigen-binding fragment or derivative thereof with CD40 agonist activity.

In a further embodiment, the second active agent is a conventional anti-cancer treatment. For example, the anti-cancer treatment may be selected from the group consisting of chemotherapeutic agents (such as gemcitabine, docetaxel), radiotherapy, surgery, cancer vaccines (such as BCG, Melacine®), adoptive T-cell transfer and $T_{reg}$ depletion therapies.

In another embodiment, the first immunomodulatory agent is for release continuously over an extended period and the second immunomodulatory agent is for release in short intermittent pulses, or vice versa.

An essential feature of the immunomodulatory agents of the first aspect of the invention is their use in the local treatment of a tumour in a patient, wherein the treatment regime comprises patient-specific optimisation of the dose of the immunomodulatory agent to identify the maximum therapeutic dose that does not induce an increase in the number of local regulatory T cells ($T_{reg}$ cells) in the patient.

By "patient-specific optimisation of the dose" we mean that the dose of the immunomodulatory agent is optimized individually for each patient.

In one embodiment, patient-specific optimisation of the dose comprises local administration to the patient of the immunomodulatory agent at different doses and measurement, after each dose, of the number of local $T_{reg}$ cells and/or the ratio of local $T_{reg}$ cells to local $T_{eff}$ cells.

By "regulatory T cells" or "$T_{reg}$ cells" we mean T cells (T lymphocytes) that regulate the activity of other T cell(s) and/or other immune cells, usually by suppressing their activity. In one embodiment, the $T_{reg}$ cells are CD4+, CD25+, FoxP3+ T-cells (but it will be appreciated by persons skilled in the art that $T_{reg}$ cells are not fully restricted to this phenotype).

By "effector T cells" or "$T_{eff}$ cells" we mean are T cells (T lymphocytes) that carry out the function of an immune response, such as killing tumor cells and/or activating an anti-tumour immune-response which can result in clearance of the tumour cells from the body. In one embodiment, the $T_{eff}$ cells are CD3+ with CD4+ or CD8+. $T_{eff}$ cells may secrete, contain or express effector markers such as IFNgamma, granzyme B and ICOS (but it will be appreciated by persons skilled in the art that $T_{eff}$ cells are not fully restricted to these phenotypes).

By "local" we mean that the $T_{reg}$ cells and $T_{eff}$ cells are in the vicinity of the tumour, i.e. at the site of the tumour.

In one embodiment, the different doses of immunomodulatory agent are administered in order from lowest to highest dose.

Of course, it will be appreciated that the assessment of the effects of each dose may involve repeated administration of that dose, optionally over several days, before the next dose is tested.

In one embodiment, the maximum therapeutic dose that does not induce an increase in the number of local $T_{reg}$ cells in the patient is identified as the dose associated with the lowest ratio of local $T_{reg}$ cells to local $T_{eff}$ cells.

After patient-specific optimisation of the dose of the immunomodulatory agent, as described above, the patient is then administered the maximum therapeutic dose for the duration of the treatment. However, it will be appreciated that the dose may be lowered over time once the treatment starts to have the required therapeutic effect.

Typically, the maximum therapeutic dose of the immunomodulatory agent in a human patient will be in the range of 0.1 to 10 mg/kg per administration. For example, the maximum therapeutic dose may be between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

In one embodiment, the maximum therapeutic dose of the immunomodulatory agent is a low dose. For example, the dose to be administered locally in the present invention may be less than 25% of the typical systemic dose of the same agent needed to produce a therapeutic effect. In one embodiment, the dose is less than or equal to 1 mg per administration, for example less than or equal to 500 μg, 400 μg, 300 μg, 200 μg, 100 μg, 50 μg, 30 μg, 20 μg, 10 μg, 5 μg or 1 μg per administration. It will be appreciated that such doses may be administered repeatedly to the patient over time, for example twice daily, once daily, once every other day, twice weekly, once weekly, twice monthly, once monthly, etc.).

In one embodiment, the immunomodulatory agent(s) is/are for use at a dose of 10 μg to 50 μg per administration.

For example, the immunomodulatory agent(s) may be used at a dose of 20 μg to 40 μg per administration, for example 30 μg per administration.

In one embodiment, the immunomodulatory agent(s) exhibit an inverse dose-therapeutic effect response.

In one embodiment, the immunomodulatory agent(s) is/are capable of providing a systemic anti-tumour effect.

In one embodiment, the immunomodulatory agent(s) is/are capable of providing a change in the ratio between effector and suppressor cells and/or mechanisms.

The relative numbers of different suppressive cell types, e.g. $T_{reg}$ cells can be measured by flow cytometry (based on CD25 and Foxp3, CD4 positivity) in different compartments, such as spleen, tumour draining lymph nodes, blood. The relative number of effector cells may be measured by flow cytometric analysis of different suppressive cell types, e.g. $T_{eff}$ cells can be measured by flow cytometry (based e.g. on CD8, CD107, IFNgamma positivity) in different compartments, such as spleen, tumour draining lymph nodes, blood, the tumour.

It will be appreciated by persons skilled in the art that the number of $T_{reg}$ cells and/or $T_{eff}$ cells may be measured at different time points after administration of the immunomodulatory agent(s). For example, the number of $T_{reg}$ cells and/or $T_{eff}$ cells may be measured on the same day as administration of the immunomodulatory agent(s) and/or several weeks (e.g. 2, 3, 4, 5, 6 7 or even 8 weeks) after administration of the immunomodulatory agent(s). Typically, however, the number of $T_{reg}$ cells and/or $T_{eff}$ cells is measured one to seven days after administration of the immunomodulatory agent(s). Thus, in one embodiment, the maximum therapeutic dose is determined as the maximum local dose that does not induce an increase in the number of local $T_{reg}$ cells in the patient 1, 2, 3, 4, 5, 6 and/or 7 days after its administration.

In one embodiment, the immunomodulatory agent(s) is/are capable of providing a change in effector or suppressor cell number and/or the ratio between these subsets, where the change correlates with the anti-tumour effects.

In one embodiment, the immunomodulatory agent(s) exhibit a favourable adverse effect profile, e.g. reduce or no autoimmune reactions (colitis, dermatitis) for CTLA-4 blockade.

In one embodiment, wherein the immunomodulatory agent(s) exhibit a reduced adverse effect profile relative to high dose application of the immunomodulatory agent In one embodiment, the immunomodulatory agent(s) exhibit a reduced adverse effect profile relative to systemic administration of the immunomodulatory agent (at a dose which provides an equivalent therapeutic effect).

It will be appreciated by persons skilled in the art that the immunomodulatory agents of the invention will be administered in the form of a pharmaceutical composition comprising an effective amount of the agent as defined herein and a pharmaceutically-acceptable diluent, carrier or excipient.

As used herein, 'pharmaceutical composition' means a therapeutically effective formulation according to the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent.

In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

The agents of the invention may be delivered using an injectable sustained-release drug delivery system. These are designed specifically to reduce the frequency of injections. An example of such a system is Nutropin Depot which encapsulates recombinant human growth hormone (rhGH) in bio-degradable microspheres that, once injected, release rhGH slowly over a sustained period. Preferably, delivery is performed intra-muscularly (i.m.) and/or sub-cutaneously (s.c.) and/or intravenously (i.v.).

The agents of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

However, the agents of the invention will typically be administered locally at or near the tumour by injection, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents of the invention can be administered alone but will generally be administered in admixture with a suitable pharmaceutical excipient, diluent or carrier selected with regard to the intended route of administration and standard pharmaceutical practice.

Medicaments and pharmaceutical compositions suitable for administration by injection include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The medicaments and pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For veterinary use, the agents of the invention are administered as a suitably acceptable formulation in accordance with normal veterinary practice and the veterinary surgeon will determine the dosing regimen and route of administration which will be most appropriate for a particular animal.

The agents of the invention may be formulated at various concentrations, depending on the efficacy/toxicity of the compound being used, for example as described in the accompanying Examples. For in vitro applications, formulations may comprise a lower concentration of a compound of the invention.

In one embodiment, the immunomodulatory agent(s) is/are provided in the form of a slow release composition.

Using a slow-release matrix for intra-tumoral delivery may provide one or more of the following benefits:
Improved efficacy
Increased duration of tissue retention
Constant concentration in target tissue
Reduced amount of mAb/ligand required for local effect compared to systemic administration
Reduced dosing frequency
Increased patient convenience (due to reduced dosing frequency); and/or
Reduced risk of systemic leakage and thus systemic side effects.

In addition, carrier particles may enable higher order cross linking of stimulatory receptors, e.g. CD40 if the ADC is immobilized on the surface of the particle. There are also potential to enhance bio-distribution and uptake of the particles e.g. by specific cells or only at low pH.

Examples of slow release particles include:
nanoparticles (e.g. poly-gammaPGA particles)
microparticles (e.g. cross-linked dextran microspheres, such as OctaDex from OctoPlus Inc
Montanid
Matrigel In one embodiment, the immunomodulatory agent(s) is/are provided in the form of a pH-stabilised composition.

In one embodiment, wherein the immunomodulatory agent(s) is/are an anti-CTLA-4 antibody or antigen-binding fragment or derivative thereof with CTLA-4 antagonist activity for chronic administration by peritumoural injection.

A second aspect of the invention provides the use of an immunomodulatory agent as defined above in the preparation of a medicament for the local treatment of tumours, wherein the treatment comprises patient-specific optimisation of the dose of the immunomodulatory agent to identify the maximum therapeutic dose that does not induce an increase in the number of local $T_{reg}$ cells in the patient.

A third aspect of the invention provides a method for the treatment of tumours in a patient comprising the step of administration to the patient of an immunomodulatory agent as defined above, wherein the immunomodulatory agent is administered locally at or in the vicinity of the tumour and wherein the method comprises patient-specific optimisation of the dose of the immunomodulatory agent to identify the maximum therapeutic dose that does not induce an increase in the number of local $T_{reg}$ cells in the patient.

A fourth aspect of the invention provides a method for determining an optimal dose of an immunomodulatory agent for the local treatment of a tumour in a patient comprising:
(a) providing a sample of cells from a patient who has received local treatment of a tumour with an immunomodulatory agent at a test dose;
(b) measuring the number of $T_{reg}$ cells in the sample of cells;
(c) repeating steps (a) and (b) at a different test dose of the immunomodulatory agent, as necessary, to determine the maximum dose of the immunomodulatory agent that does not induce an increase in the number of $T_{reg}$ cells in the sample, wherein the optimal dose is determined as the maximum dose of the immunomodulatory agent that does not induce an increase in the number of $T_{reg}$ cells.

In this respect, it will be appreciated by persons skilled in the art that the expression "does not induce an increase in the number of $T_{reg}$ cells" (as used herein) is intended to encompass doses that may increase the number of $T_{reg}$ cells in the sample to some extent but not sufficiently to have a substantive inhibitory effect on the patient's immune response to tumour cells.

In one embodiment, the sample of cells is selected from the group consisting of blood samples, tumour biopsies and tumour draining lymph node biopsies. Thus, the method may comprise determination of the effect of the test dose of the immunomodulatory agent on local $T_{reg}$ cells, i.e. at or in the vicinity of a tumour.

In one embodiment, the method further comprises measuring the number of effector cells in the sample of cells in step (b), wherein the optimal dose is determined as the dose of the immunomodulatory agent that induces a maximal increase in the number of effector cells in the sample without inducing an increase in the number of $T_{reg}$ cells.

In one embodiment, the maximum therapeutic dose that does not induce an increase in the number of local $T_{reg}$ cells in the patient is identified as the dose associated with the lowest ratio of local $T_{reg}$ cells to local $T_{eff}$ cells.

In one embodiment, the method further comprises, prior to step (a), determination of baseline measurements of $T_{reg}$ cells and/or $T_{eff}$ cells in a sample of cells from the patient prior to administration of any dose of the immunomodulatory agent.

In another embodiment, the immunomodulatory agent is as defined above.

A fifth aspect of the invention provides the use of $T_{reg}$ cells as a marker of the efficacy of the treatment of a tumour in a patient with an immunomodulatory agent.

A sixth aspect of the invention provides the use of the ratio between $T_{reg}$ cells and T effector cells, or of the ratio between molecules mediating immune activation and suppression, as a marker of the efficacy of the local treatment of a tumour in a patient with an immunomodulatory agent.

In one embodiment of the fifth and sixth aspects of the invention, the treatment of a tumour comprises local administration of a CTLA-4 inhibitor (at or near the tumour site).

In a further embodiment, the immunomodulatory agent is as defined above.

As used herein, the singular forms "a", "and", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

The listing or discussion in this specification of an apparently prior-published document should not necessarily be taken as an acknowledgement that the document is part of the state of the art or is common general knowledge.

Exemplary embodiments of the invention are described in the following non-limiting examples, with reference to the following figures:

FIG. 1: To elucidate the optimal concentration of locally administered aCTLA-4 in vivo we set up a dose response experiment using (A) 3×PBS (B) 3×30 µg, (C) 3×60 µg and (D) 3×90 µg. Therapy took place on d5, d8 and d11 after inoculation of $2.5×10^5$ Panc02 cells subcutaneously. CR=complete regression, p.t.=peritumoral FIG. 2: Animals were treated two times with 30 µg or 90 µg local aCTLA-4, on d5 and d8 after tumour inoculation. (A) The amount of $T_{reg}$ cells CD4+, CD25+, FoxP3+) in spleen were quantified by FACS analysis on d11 and there were a significant increase in this population in mice receiving the higher dose of aCTLA-4 (mean *p<0.05). (B) To test their functionality, $T_{reg}$ cells (CD4+ CD25+) were isolated from spleen on d11 and were mixed at different ratios against responder cells (CD4+ CD25−) for two days. $T_{reg}$ cells in all treatment groups showed a dose-dependent inhibition of proliferation of responder cells. Data represent one out of two representative experiments with 3 mice/group (mean±SEM).

Figure 3:
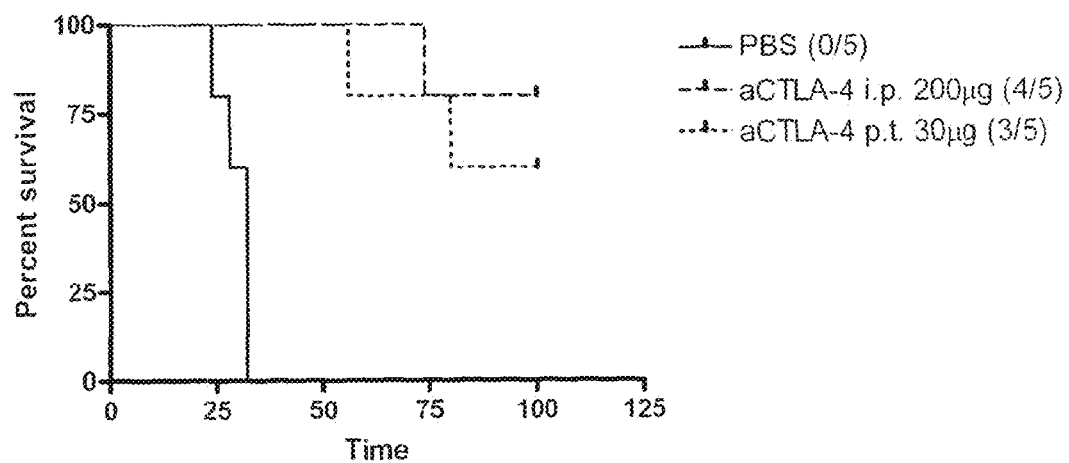

FIG. 3: Mice received subcutaneous injections of $2.5×10^5$ Panc02 cells on d0 and treatment with aCTLA-4, 200 µg/dose i.p. and 30 µg/dose p.t., on d5, d8 and d11. Prolong survival in animals carrying an experimental pancreatic tumour even at a dose that is seven times lower than the systemically injected dose. Data represent cumulative results from two individual experiments (p<0.0001 i.p. or p.t. aCTLA-4 compared to PBS control).

FIG. 4. Local aCTLA-4 induces systemic anti-tumour effects. A two-tumour model was established where either (A) $2.5×10^5$ Panc02 cells or (B) 3×105 MB49 cells were inoculated in each flank of animals. Treatment with local (30 µg) aCTLA-4 took place d5, d8 and d11 in the Panc02 model and d8, d11 and d14 in the MB49 model.

FIG. 5: Several autoimmune side effects were evaluated in Panc02 tumour bearing mice injected with 3×200 µg systemic and 3×30 µg local administration of aCTLA-4 therapy. Tumour inoculation with $2.5×10^5$ Panc02 started on d0 and therapy on d5, d8 and d11. (A) Plasma was taken from mice on d15 and anti-nuclear antibodies (ANA) were measured by ELISA. (B) the weight of spleen was noted four days after the last treatment (d14) (C) Representative histological sections of gastro-intestines. 1) Normal gastric mucosa of a PBS treated mouse. 2) Animal receiving systemic aCTLA-4 therapy. The forestomach (left) is normal, but the glandular mucosa adjacent the limiting ridge is markedly thickened, displaying a plaque-like change (arrows) of mucosal hypertrophy and hyperplasia. The basal part of the mucosa and submucosa under the lesion are focally infiltrated by leukocytes (asterisk). Compare mucosa thickness in the plaque with the normal gastric mucosa (right). 3) Detail of the plaque-like change in 2) (asterisk). The lamina propria at the base of the gland and the submucosa exhibit numerous infiltrating leukocytes, predominantly neutrophils. 4) Detail of the plaque-like change in 2). The neck of the glands appears disorganized at sites, displaying scattered mitoses (arrows). Four out of five animals in the i.p. group, one out of five in the p.t. group and one out of five in the control group experienced acute gastritis (n=5).

FIG. 6. Animals were challenged with $2.5×10^5$ Panc02 cells and treated with local injections of 30 µg aCTLA-4 and/or 30 µg a41BB on day 5, 8 and 11. (A) mean tumour growth in the different treatment groups. (B) survival.

FIG. 7. Ratio between T effector cells and $T_{reg}$ cells in (A and B) TDLN and (C and D) tumor. Both CD4 (A and C) and CD 8 (B and D) effector cells are shown.

FIG. 8. Quantification of MdSC in (A) TDLN and (B) tumor. (C) PDL-1 expression on CD45− cells (mostly tumour cells) after the different therapies.

Figure 9:
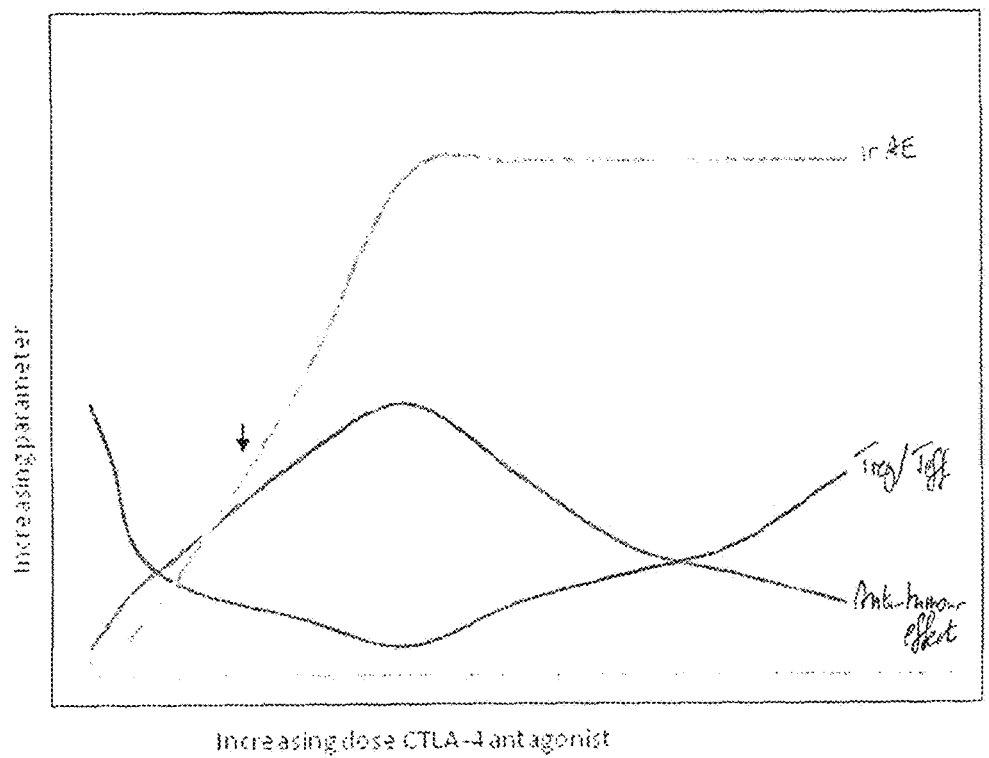

FIG. 9. The relationship between anti-tumour effect, $T_{reg}$ cell/$T_{eff}$ cell ratio and toxic effects (irAE) following systemic administration of increasing doses of a CTLA-4 blocking agent.

Figure 10:
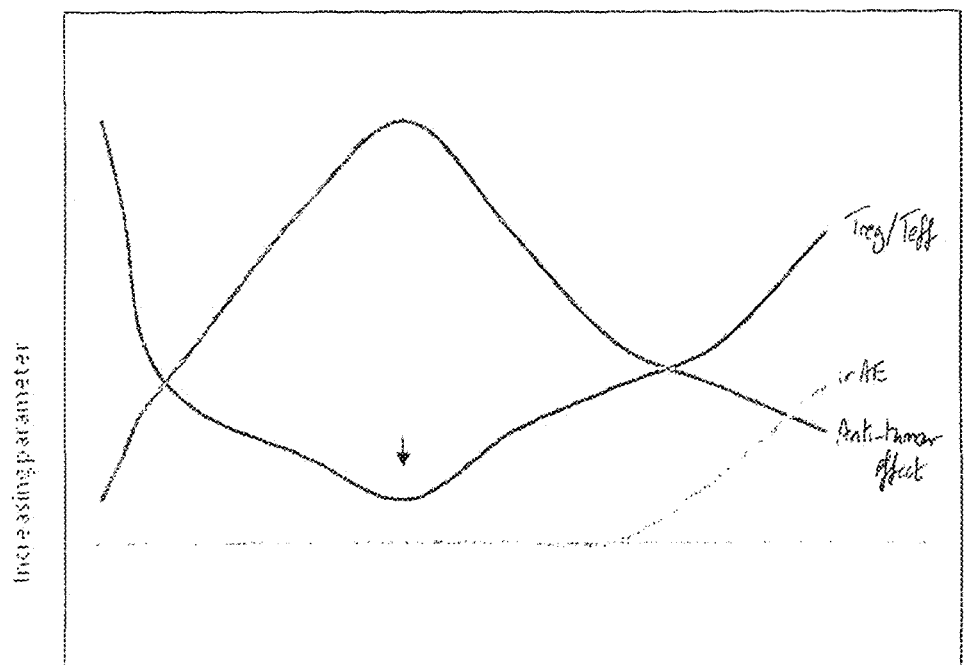

FIG. 10. The relationship between anti-tumour effect, $T_{reg}$ cell/$T_{eff}$ cell ratio and toxic effects (irAE) following local administration of increasing doses of a CTLA-4 blocking agent.

EXAMPLE A

Materials and Methods

Cell Lines

Panc02 cells (murine ductal adenocarcinoma) were kindly provided by Dr. R. Heuchel (Karolinska University Hospital, Sweden). The cells were cultured in DMEM+ GlutaMax supplemented with 10% FBS, 1 mM sodium pyruvate, 100 U/ml Penicillin and 100 U/ml Streptomycin (Gibco) and were incubated in 37° C. at 5% $CO_2$. The Panc02 cell line was established in 1984 through chemical induction by implantation of cotton thread-carrying 3-methyl-cholanthrene into the pancreas tissue of female C57BL/6 mice. It is highly insensitive to a wide range of cytotoxic agents thus mimicking its human counterpart. The murine bladder cancer cell line MB49 (Mouse Bladder-49; a kind gift from Dr. K. Esuvaranathan, National University of Singapore, Singapore) was cultured under similar conditions with the exception of 0.1 mM sodium pyruvate and 7% $CO_2$. MB49 is a carcinogen-induced transitional cell carcinoma derived from a C57BL/6 male mouse.

Animals

Female C57Bl/6 mice were obtained from Scanbur B&K (Sollentuna, Sweden) weighing 18-20 g at experiment initiation. Animals were housed at the Rudbeck Animal Facility and cared for by the staff according to local regulation. All animal experiments were approved by the local Animal Ethics Committee (Dnr: C91/8, C163/8).

Therapeutics

Antagonistic mouse-anti-mouse CTLA-4 antibodies (clone: 9D9) were purchased from Bio X Cell (West Lebanon, N.H., USA). Antibodies were diluted in PBS to stock solutions ten times higher than the effective dose; 2 mg/ml for intraperitoneal (i.p.) injections, 0.3 mg/ml, 0.6 mg/ml or 0.9 mg/ml for peritumoral (p.t.) injections.

In combination therapy experiments, the following therapeutics were used: Rat IgG (BioLegend, San Diego, Calif., USA), hamster-α-mouse CTLA-4, clone: 9H10 (BioLegend, San Diego, Calif., USA) and rat-α-mouse 4-1BB, clone: 3H3 (kindly provided by R Mittler, Yerkes Research Center, Atlanta, Ga., USA)

In Vivo Experimental Design

To mimic PDAC in a murine model, $2.5 \times 10^5$ Panc02 cells were inoculated subcutaneously (s.c.) in the right hind leg of female C57BL/6 mice on day 0. In experiments investigating the distant effect of the same tumor, $2.5 \times 10^5$ Panc02 or $3 \times 10^5$ MB49 cells were injected in both the right and the left flank, respectively, of individual animals. 100 µl of antibody stock solution/dose (i.p.: 200 µg, p.t.: 30 µg, 60 µg or 90 µg per mouse) was administered three or six times with a three-day interval. Therapy started on day 5 after tumour injection for the Panc02 model and on day 8 for the MB49 model. The same number of cells, $2.5 \times 10^5$ Panc02 and MB49 was inoculated in respective flank of the same animal in an experiment studying the distant effect on an irrelevant tumor. Therapy started on day 5 for this tumour model, otherwise using the same dosage schedule as described earlier. Tumour growth and survival was monitored throughout the experiment. Tumour volume was measured with caliper and calculated by the ellipsoid volume formula: $=4/3*\pi*a(length)*b(width)*c(depth)$. For rechallenge experiments, mice were injected with $2.5 \times 10^5$ Panc02 cells in the opposite flank to the initial growth site and observed over time. Mice were sacrificed if the tumour exceeded 1 $cm^3$ or if ulcers developed.

For the combination therapy tumour challenge was made day 0 with $2.5 \times 10^5$ Panc02 cells injected s.c. Local treatment with 30 µg aCTLA-4 (CD152) blocking antibody and/or 30 µg a41BB (CD137) agonist antibody every 3rd day (day 6 and day 9). Animals were sacrificed at day 13 and blood, tumour draining lymph node (TDLN) and tumour were isolated.

FACS Analysis

To quantify $T_{reg}$ cells in the spleen and the tumour draining lymph node (TDLN), cells were stained for surface receptors CD4 (BioLegend) and CD25 (BD Bioscience) and stained intracellular for FoxP3 (BioLegend), according to the manufacturer's protocol. Samples were analyzed with a FACSCalibur or LSRII (BD Biosciences) flow cytometer. Data analysis was performed with FlowJo software (TreeStar).

Functional $T_{reg}$ Cell Suppression Assay

Animals were subjected to two treatments with peritumoral aCTLA-4 on day 5 and 8 after tumour inoculation. Three days after the last treatment (d11) mice were euthanized and spleens were isolated from animals in the following groups: PBS, 30 µg and 90 µg aCTLA-4. Splenocytes were isolated by mashing spleens against a MESH membrane (70 µm, BD Bioscience) twice. The membrane was washed with PBS and red blood cells were lysed in the collected single cell suspension (Pharm Lyse, BD Bioscience Pharmingen). Regulatory T cells ($T_{reg}$ cells) were purified by first negative selection of CD4+ cells (MACS, Milteny) and subsequently positive selection of CD25+ cells (MACS, Milteny) according to the manufacturer's protocol. The enriched $T_{reg}$ cell population contained between 39-55% $T_{reg}$ cells when stained for CD4 and CD25. 85-95% of these $T_{reg}$ cells were FoxP3+. Isolated $T_{reg}$ cells from three animals were pooled to achieve enough material. CD4+ CD25− splenocytes (responder cells), from naïve mice were isolated as described above and labeled with 5 µM CFSE according to manufacturer's protocol. Three different $T_{reg}$ cell to responder cell ($T_{resp}$) ratios were set up for the different treatment groups in a 96-well plate. The cells were incubated in R10 medium (RPMI 1640, 100 U/ml Penicillin and 100 U/ml Streptomycin, 10 mM HEPES, 50 µM β-mercaptoethanol (Gibco) and 10% FBS) supplemented with 1 µg/ml aCD3 (Pharmingen, clone: 17A2) and 2 µg/ml aCD28 (BioLegend, clone: E18) for 2 days in 37° C. and 5% $CO_2$ before FACS analysis. Cells were stained for CD3 expression and the percentage of proliferating CD3+ cells was determined.

Investigation of Autoimmune Events

Anti-nuclear antibodies (ANA) in plasma were detected with ANA ELISA kit (USBiological, Swampscott, Mass.) according to the manufacturer's protocol. Blood was collected by tail veil incision or by heart puncture into tubes containing heparin. Plasma was stored at −80° C. Samples were run in duplicates and ANA levels were considered positive if levels were twice the naïve control. Target organs were isolated and fixed in 4% formaldehyde before imbedded in paraffin. Sections (5-10 µm) were stained with H&E and evaluated for leukocyte infiltration by an experienced pathologist. All samples were blinded for optimal objectivity. Photographs were taken using a Nikon E600 microscope and Nikon Digital Camera DXM 1200 (Japan).

Statistical Analysis

Statistical analyses were performed using GraphPad prism version 4.03 software (GraphPad Software, Inc., CA, USA).

Results

Local aCTLA-4 is Effective, but Increasing the Dose does not Improve Therapy

Anti-CTLA-4 (aCTLA-4) therapy has mostly been applied systemically by i.v. or i.p. injection, and the two published investigations with local aCTLA-4 therapy were experiments with cell lines expressing aCTLA-4 antibody in combination with $T_{reg}$ cell inhibition[19] or in combination with GM-CSF expressing tumours[24]. Local administration of a single high dose of aCTLA-4 was reported ineffective[19]. We hypothesized that local aCTLA-4 might have a regular dose-response curve and set up an experiment with established Panc02 tumours that were treated with three different doses of aCTLA-4. Starting on day 5, 30 µg, 60 µg or 90 µg of aCTLA-4 was injected p.t. every third day and repeated for at total of three times. As illustrated in FIG. 1 no clear dose-response curve was seen upon local therapy. Rather the highest dosage (90 µg) of antibody appeared less effective than the lowest dose of 30 µg.

$T_{reg}$ Cells Levels Increase Further in Mice Receiving a Higher Dose of Local aCTLA-4

One hypothesis as to why a higher dose of aCTLA-4 is not more beneficial to therapy might be that 90 µg of aCTLA-4 is just above the threshold to induce local $T_{reg}$ cells. In order to test this, we isolated $T_{reg}$ cells from spleens of mice that received two doses of 30 µg and 90 µg aCTLA-4 therapy, respectively. The numbers as well as function of $T_{reg}$ cells were investigated ex vivo. As depicted in FIG. 2A, there was a significant increase in $T_{reg}$ cells upon increased dosing of aCTLA-4 (mean *p<0.05). $T_{reg}$ cell capacity to suppress responder cells (CD4+ CD25− splenocytes from naïve mice) was equally effective in all treatment groups (FIG. 2B, mean±SEM). Control cells (CD4+ CD25− from treated animals) were also investigated for their suppressive capacity but did not display any proliferative inhibition of responder cells (data not shown). Therefore, higher doses of local aCTLA-4 induced functional $T_{reg}$ cells in this experimental model. Thus, 30 μg aCTLA-4 appeared optimal both from a therapeutic as well as from a cost-benefit perspective.

Comparison of Local and Systemic aCTLA-4 Therapy

Since the lowest dose of aCTLA-4 was therapeutically efficient, we went further to compare 30 μg locally injected aCTLA-4 to a previously proven effective systemic dose of 200 μg aCTLA-4 (Mangsbo et al., 2010, *J. Immunother* 33(3): 225-235). Injections took place three days apart, on d5, d8 and d11 after tumour inoculation. Both systemic and local administration produced efficient anti-tumour effects compared to PBS-treated animals (Not shown). Long-term survival paralleled the results from tumour measurements, and both local as well as systemic aCTLA-4 therapy prolonged survival (FIG. 3, ***p<0.0001 i.p. or p.t. aCTLA-4 compared to PBS control). To investigate if cured mice irrespectively of treatment route exhibited tumour immunity, we performed a rechallenge on mice and observed complete Panc02 tumour rejection. Thus, tumour immunity was demonstrated after both systemic and local aCTLA-4 administration (data not shown).

Local aCTLA-4 Therapy Generates Anti-Tumour Effects on Distant Tumours

Since tumour immunity was demonstrated upon rechallenge in mice treated with local aCTLA-4, we hypothesized that local therapy induces systemic anti-tumour effects. To investigate this, a tumour model was set up where tumours grew on both the right and left flank of individual mice. Two different experimental models were used; Two Panc02 tumours or two MB49 tumours on each mouse, and only the right side tumour was subjected to p.t. aCTLA-4 injections. Dosing regimen was identical to the previous experiment for the Panc02 model, whereas treatment of the MB49 model took place on d8, d11 and d14. Tumour sizes were measured and tumour reduction was observed for both tumours on the same mouse after local treatment (most prominent in the MB49 model) as shown in FIG. 4.

In another 2-tumour model, two different tumour types were inoculated on the same animal. Thus, Panc02 cells were injected in the right flank while MB49 cells grew in the left flank. The same dosing regimen was applied as described in Materials and Methods. Interestingly, local aCTLA-4 treatment of the Panc02 tumour on the right side significantly reduced tumour growth of the MB49 tumour on the left side (d25*p<0.05 local treatment of MB49 tumour compared to PBS, **p<0.01 treatment of Panc02 tumour on opposite side compared to PBS).

Reduced Autoimmune Events with Local CTLA-4 Blockage

Adverse side effects in the form of autoimmunity are common when interfering with T cell tolerance using aCTLA-4 therapy. Since the two different treatment regimens both induced systemic anti-tumour effects it was important to investigate whether local injection could reduce side effects compared to systemic injection with a maintained anti-tumour effect. For this purpose, animals were treated as previously with 30 μg local aCTLA-4 injections or 200 μg systemic aCTLA-4 administration for three times with three day intervals. Animals were sacrificed four days after the last treatment and various analyses were performed: ANA, immunohistochemistry of target organs, ALAT levels, as well as spleen, TDLN and thymus weight. ANA levels were considered positive if two times that of naïve control mice. FIG. 5A illustrates that five out of ten mice treated with systemic aCTLA-4 demonstrated positive ANA levels while only two out of ten locally treated mice displayed a positive ANA. In the PBS control group no animals had positive ANA (p<0.05, Chi-square test, contingency table with all groups; ANA versus no ANA). An increase in spleen weight was seen in the group treated with systemic injections compared to the control group (*p<0.05, unpaired t-test, n=4) FIG. 5B. This increase in weight was not present in mice treated with low dose local aCTLA-4 (p>0.1, unpaired t-test). Four out of five mice in the i.p. group, one out of five in the local aCTLA-4 group and one out of five in the control group displayed gastritis FIG. 5C. The etiology of this gastritis has not been determined, but "spontaneous" gastritis is uncommon in mice.

Combination Therapies

Unfortunately, the dose-response experiment limits any attempt to further increase the aCTLA-4 dose but opens up for the opportunity to perform combination therapies that include the low-dose aCTLA-4 schedule Tumour Growth and Survival In these experiments both antagonistic (a-CTLA-4) and agonistic (a-4-1BB) antibodies were used for treatment of established Panc02 tumours. 4-1BB (CD137) belongs to the TNFR super family and is expressed by activated T cells, NK cells and DCs. Its ligand 4-1BBL (CD137L) is present on activated APC and in tissue. We hypothesized that using a combination of antibodies that stimulate T effector cells as well as block inhibitory checkpoints would further enhance antitumour therapy. FIG. 6 shows a reduction in tumour burden as well as an increase in overall survival with the combination of agonist plus antagonist treatment compared to any individual treatment.

Ratio Between T Effector and $T_{reg}$ Cells

The aim of tumour immunotherapy is to tilt the dominance of suppressive mechanisms ($T_{reg}$ cells, IL-10, TGFb etc.) towards effector mechanisms (e.g. CD8, IFNg etc.). This is hopefully done by increasing the levels of effector cell types/ molecules and/or reducing the levels of suppressor cells/molecules. By investigating such effector/suppressor ratios in the tumor, TDLN, spleen and blood in may be possible to objectively visualize the immune effects of different treatments and to predict tumour outcome. FIG. 7 show a clear trend of immune activation in both TDLN and tumour when combining a stimulatory and blocking antibody in this tumour model. The therapeutics used for this set of experiments were: Rat IgG (BioLegend, San Diego, Calif., USA), mouse-α-mouse CTLA-4, clone: 9D9 (Bio X Cell, West Lebanon, N.H., USA) and rat-α-mouse 4-1BB, clone: 3H3 (kindly provided by R Mittler, Yerkes Research Center, Atlanta, Ga., USA).

Effects on Other Suppressor Cell Types

One common suppressive cell type found in pancreatic cancer are the myeloid-derived suppressor cells (MdSC), here defined as CD11b+ Gr-1+. MdSC can induce a suppressive microenvironment within the tumour by secretion of inhibitory cytokines (e.g. IL 10, TGFβ), metabolic deprivation of T cells (e.g. arginase-1, NOS, IDO) and stimulation of other suppressive cell types (e.g. $T_{reg}$ cells, Th17).

The FIG. 8 shows quantification of MdSC in (A) TDLN and (B) tumor. It appears that regimens containing a41BB±aCTLA4 elevate MdSC in the LN, whereas aCTLA4 alone does not. In contrast, the combined antibody regimen does not elevate MdSC numbers in the tumour above PBS control.

PD-L1 is an important regulator for peripheral tolerance and is expressed on both immune cells, non-hematopoietic cells and on many tumours. PD-L1 binds to PD-1 on T cells, thereby delivering a negative signal. It is believed that solid tumours utilize PD-L1 as an escape mechanism, and this molecule is up-regulated upon IFNγ stimulation. The FIG. 8C demonstrates PD-L1 expression on CD45− cells (mostly tumour cells) after the different therapies. The fact that the most powerful anti-tumour combination of a41BB+aCTLA4 yielded the highest expression of PD-L1 on CD45− (epithelial, tumor) cells may reflect local release of IFNg by activated T cells.

Discussion

Anti-CTLA-4 therapy has previously been found effective in different murine tumour models. However, a deeper investigation into systemic effects induced by local peritumoral inhibition of this important immune check-point has not been performed. Hence, we decided to evaluate the effects of local aCTLA-4 therapy in two different tumour models with focus on an experimental pancreatic tumour model. Surprisingly, we found that increasing amounts of aCTLA-4 yielded an inverse dose-response curve. When evaluating $T_{reg}$ cells in the spleen of animals treated with 30 μg or 90 μg of aCTLA-4 we found more functional cells of this type after the higher dose. Kavanagh et al. reported that systemic aCTLA-4 administration leads to elevated $T_{reg}$ cell levels in humans in a dose-dependent manner[25]. Such data could help to explain our inverse correlation between dose and tumour growth curves in FIG. 1 and the increased $T_{reg}$ cell population (FIG. 2). Thus, local blockade could lead to high concentrations of aCTLA-4 at the tumour area with local $T_{reg}$ cell accumulation as a consequence. Inverse or J-shaped dose-response curves do exist and radiation therapy is one example. Low dose radiation primarily eradicates suppressor cells while a high dose leads to systemic immune suppression with tumour progression as a possible consequence.

Since 30 μg of aCTLA-4 per dose administrated three times resulted in clear anti-tumour responses, this therapy was compared to a known effective dose of systemically administrated aCTLA-4 (Mangsbo et al., submitted manuscript). Local administration was equally potent as systemic aCTLA-4 therapy in tumour reduction and survival, but at a dose seven times lower (FIG. 3). Unfortunately, the dose-response experiment limits any attempt to further increase the aCTLA-4 dose but opens up for the opportunity to perform combination therapies that include the low-dose aCTLA-4 schedule.

To evaluate if local therapy had an effect on distant tumours, we tested two different twin-tumour models where mice were inoculated with one tumour on each flank. In the first experiment we had mice each carrying two Panc02 tumours or two MB49 tumours and the effect of i.p. versus p.t. aCTLA-4 therapy was assessed.

Since systemic effects were demonstrated with local therapy, we proceeded to analyze possible adverse effects by local or systemic aCTLA-4 therapy. Anti-CTLA-4 administration in humans revealed that patients may experience autoimmune side effects. Anti-nuclear antibodies have been detected post treatment. Autoimmune adverse events appear to correlate with improved overall survival but this is currently a matter of debate[26]. Since we have established an anti-tumour effect with local aCTLA-4 therapy we sought to elucidate if toxicity was diminished compared to systemic treatment. Indeed we did not observe splenomegaly nor increased ANA levels post local aCTLA-4 therapy, both of which were detected after systemic therapy (FIG. 5). In addition, mice treated with systemic aCTLA-4 therapy demonstrated acute gastritis in four out of five mice as opposed to one out of five mice in both the PBS and the local treatment groups. The fact that mice treated with local CTLA-4 blockade had reduced side effects has also been shown by Simmons and colleagues[24], however with a tumour secreting aCTLA-4 antibody.

Two different groups have assessed the possibility to use CTLA-4 antibody expressing tumour cells. Tuve et al[19] described cloning of the heavy and light chain from the hybridoma UC10-4F10-11 (hybridoma producing hamster aCTLA-4 antibody) and demonstrated the need for local continuous production of aCTLA-4 for effective therapy and long-lasting anti-tumour memory. They also administrated hamster aCTLA-4 systemically and locally but claimed no significant effect on tumour growth. This is in stark contrast to our present data which show a strong therapeutic effect both after systemic and local aCTLA-4 therapy. Factors that could account for these discrepant outcomes are the tumour model, treatment schedule, dosing and antibody clones. The systemic long-time (10 times during 29 days, 150 μg each time) administration of a hamster antibody may allow for neutralizing anti-hamster antibody production and drug elimination. In addition, a high-dose of 200 μg aCTLA-4 in the tumour area might not be the optimal dosing as FIG. 1 demonstrates that elevated local dosages resulted in inferior anti-tumour effects. Simmons et al[24] applied the same clone (clone 9D9, mouse anti-mouse CTLA-4 antibody) as used by us and demonstrated a clear anti-tumour effect post local treatment with two doses of aCTLA-4 combined with irradiated GM-CSF-expressing tumour cells. However, they did not investigate how the low local dose aCTLA-4 alone affected tumour growth.

Our data demonstrate in two different tumour models that it is possible to apply aCTLA-4 antibodies at low dose peritumorally with few side effects but with a systemic anti-tumour effect. The current observations stress the importance of confirming the optimal dosing schedule for this type of therapy in the clinic since our data signify a complex dose-response relationship.

Reversion of the suppressive tumour milieu may result in an increase in effector cells, mainly cytotoxic T lymphocytes, and a reduction of suppressive immune cells, e.g. $T_{reg}$ cells. Interestingly, we found that the percentage of $T_{reg}$ cells among the T cell population in the spleen was lower in the local low dose treatment group then the local higher dose treated group (FIG. 2). Thus, the lower $T_{reg}$ cell percentage resulting from the lower locally administrated dose correlates with a better anti-tumour effect (FIG. 1). This correlation between the local dose administered, and the biomarker (the $T_{reg}$ cell ratio), which in turn (inversely) correlated with the overall survival (anti-tumour efficacy) that was discovered may be very important. Firstly, it may be valuable for determining the optimal dose regime of local anti-tumour treatment methods. It may, furthermore, also be used as a dynamic biomarker (and surrogate endpoint in clinical trials) to monitor the therapeutic efficacy of a local immunotherapeutic intervention/approach/method.

Breaking tumour tolerance and converting the suppressive tumour milieu may require immune modulation of more than one immune checkpoint regulator. It has recently been demonstrated that combinations of different immunoregulators using systemic, high dose treatment is more effective than the corresponding monotherapies (reviewed by[3, 27, 28]). The combinatorial trials with immunoregulatory therapy include 1) combination with established therapy and 2) combinations between different immunoregulator targets. However, when it comes to local immunoregulatory treatment, only very few combinations have been evaluated in a local setting (Jackaman et al and Simmons). We hypothesize that treatment using a low dose regimen comprised of a protein drug blocking an immune checkpoint regulator in combination with immune stimulating molecule would be lead to improved patient benefits (higher anti-tumour efficacy and lower toxicity). This may be particularly effective when both the blocking molecule and the immune-stimulatory molecule target a co-receptor, which has not been previously evaluated in a local immunotherapy setting.

It is conceivably that a slow-release matrix and/or carrier particle would further improve the combinatorial low dose local anti-tumour immunotherapy described herein. In fact, slow release matrix and/or carrier particles are particularly suited for the local low dose immunotherapy treatment and may improve efficacy due to increased duration of a controlled concentration of the therapeutic molecule. It may reduce dosing frequency and thereby increase patient convenience and, furthermore, minimize the risk of systemic leakage and thus systemic side effects. In addition, carrier particles may enable higher order cross linking of stimulatory receptors, e.g. CD40 if the therapeutic protein is immobilized on the surface of the particle. There are also potential to enhance bio-distribution and uptake of the particles, e.g. by specific cells or only at specific pH.

Nanoparticles, i.e. particles with a diameter of approximately 100 nm, are novel tools with great potential in the field of immunotherapy. They can be used as efficient transporters of proteins either attached to the surface or encapsulated within the particles. Different nanoparticle variants have shown great potential, both for sustained release of carried biomolecules and for activation of antigen presenting cells for induction of a cytotoxic T lymphocyte (CTL) response ($^{29}$). Recently, a novel protein delivery system based on self-assembled amphiphilic polymeric poly (γ-glutamic acid) (γ-PGA) particles, have been developed. Compared to previously developed nanoparticles, they have a high encapsulation efficacy, they are stable (can be stored freeze dried), and these nanoparticles may provide excellent carriers for the immunotherapeutic treatment described herein.

REFERENCES

1. Stagg, J., Johnstone, R. W., & Smyth, M. J. From cancer immunosurveillance to cancer immunotherapy. Immunol Rev. 220:82-101, 82-101 (2007).
2. Melief, C. J. Cancer immunotherapy by dendritic cells. Immunity. 29, 372-383 (2008).
3. Melero, I., Hervas-Stubbs, S., Glennie, M., Pardoll, D. M., & Chen, L. Immunostimulatory monoclonal antibodies for cancer therapy. Nat Rev Cancer. 7, 95-106 (2007).
4. Waldmann, T. A. Effective cancer therapy through immunomodulation. Annu. Rev Med. 57:65-81, 65-81 (2006).
5. Khawli, L. A., Hu, P., & Epstein, A. L. Cytokine, chemokine, and co-stimulatory fusion proteins for the immunotherapy of solid tumours. Handb. Exp. Pharmacol. 181: 291-328 (2008).
6. Berinstein, N. L. Enhancing cancer vaccines with immunomodulators. Vaccine. 25 Suppl 2:B72-88, B72-B88 (2007).
7. Mellor, A. L. & Munn, D. H. Creating immune privilege: active local suppression that benefits friends, but protects foes. Nat Rev Immunol. 8, 74-80 (2008).
8. Totterman, T. H., Loskog, A., & Essand, M. The immunotherapy of prostate and bladder cancer. BJU. Int. 96, 728-735 (2005).
9. Waldmann, T. A. Effective cancer therapy through immunomodulation. Annu. Rev Med 57, 65-81 (2006).
10. Shaker, M. A. & Younes, H. M. Interleukin-2: Evaluation of routes of administration and current delivery systems in cancer therapy. J Pharm Sci. 98(7):2268-98 (2009).
11. Den, O. W. et al. Local therapy of cancer with free IL-2. Cancer Immunol Immunother. 57, 931-950 (2008).
12. De Groot, C. J., Cadee, J. A., Koten, J. W., Hennink, W. E., & Den, O. W. Therapeutic efficacy of IL-2-loaded hydrogels in a mouse tumour model. Int. J. Cancer. 98, 134-140 (2002).
13. van Mierlo, G. J. et al. CD40 stimulation leads to effective therapy of CD40(−) tumours through induction of strong systemic cytotoxic T lymphocyte immunity. Proc. Natl. Acad. Sci. U.S.A. 99, 5561-5566 (2002).
14. van Mierlo, G. J. et al. Activation of dendritic cells that cross-present tumor-derived antigen licenses CD8+ CTL to cause tumour eradication. J Immunol 173, 6753-6759 (2004).
15. Jackaman, C. et al. Deliberately provoking local inflammation drives tumours to become their own protective vaccine site. International immunology. 20, 1467-1479 (2008).
16. Davis, S. J. et al. The nature of molecular recognition by T cells. Nat. Immunol. 4, 217-224 (2003).
17. Lee, K. M. et al. Molecular basis of T cell inactivation by CTLA-4. Science 282, 2263-2266 (1998).
18. Kwon, E. D. et al. Manipulation of T cell costimulatory and inhibitory signals for immunotherapy of prostate cancer. Proc. Natl. Acad. Sci. U.S.A. 94, 8099-8103 (1997).
19. Tuve, S. et al. Combination of tumour site-located CTL-associated antigen-4 blockade and systemic regulatory T-cell depletion induces tumor-destructive immune responses. Cancer Res. 67, 5929-5939 (2007).
20. van Horssen, R., Ten Hagen, T. L., & Eggermont, A. M. TNF-alpha in cancer treatment: molecular insights, antitumour effects, and clinical utility. Oncologist. 11, 397-408 (2006).
21. van Herpen, C. M. et al. Intratumoral rhIL-12 administration in head and neck squamous cell carcinoma patients induces B cell activation. Int. J. Cancer 123, 2354-2361 (2008).
22. van Herpen, C. M. et al. Pharmacokinetics and immunological aspects of a phase Ib study with intratumoral administration of recombinant human interleukin-12 in patients with head and neck squamous cell carcinoma: a decrease of T-bet in peripheral blood mononuclear cells. Clin Cancer Res 9, 2950-2956 (2003).
23. Johnson, E. E. et al. Intratumoral immunocytokine treatment results in enhanced antitumour effects. Cancer Immunol Immunother. 57, 1891-1902 (2008).
24. Simmons, A. D. et al. Local secretion of anti-CTLA-4 enhances the therapeutic efficacy of a cancer immunotherapy with reduced evidence of systemic autoimmunity. Cancer Immunol Immunother 57, 1263-1270 (2008).
25. Kavanagh, B. et al. CTLA4 blockade expands FoxP3+ regulatory and activated effector CD4+ T cells in a dose-dependent fashion. Blood 112, 1175-1183 (2008).
26. Yang, J. C. et al. Ipilimumab (anti-CTLA4 antibody) causes regression of metastatic renal cell cancer associated with enteritis and hypophysitis. J Immunother 30, 825-830 (2007).

27. Melero, I. et al. Palettes of vaccines and immunostimulatory monoclonal antibodies for combination. Clin Cancer Res 15, 1507-1509 (2009).
28. Zhang, T. & Herlyn, D. Combination of active specific immunotherapy or adoptive antibody or lymphocyte immunotherapy with chemotherapy in the treatment of cancer. Cancer Immunol Immunother 58, 475-492 (2009).
29. Akagi, T., Wang, X., Uto, T., Baba, M., & Akashi, M. Protein direct delivery to dendritic cells using nanoparticles based on amphiphilic poly(amino acid) derivatives. Biomaterials 28, 3427-3436 (2007).

EXAMPLE B

Introduction

Malignant melanoma and renal cell carcinoma have been in focus for immunotherapy because of their inherent immunogenicity and the poor response to conventional treatment.

Current research is focused on how to revert the immunosuppressive tumor micro milieu, using immunotherapeutic strategies aiming at:
1) activating professional antigen presenting cells (APC) such as dendritic cells (DC) via e.g. CD40, CD137 or Toll-like receptors (TLR),
2) using cytokines, such as IL-2, IL-12 and interferons to stimulate the lymphocytes, or
3) blocking signals that suppress T cell activation by targeting e.g. Cytotoxic T-Lymphocyte Antigen 4 (CTLA-4) or inhibitory receptor programmed death 1 (PD-1)[1-8].

By binding to CTLA-4 and blocking its interaction with B7-1/B7-2, the signaling pathway that normally inactivates T cells is blocked. Thereby, tumor specific T cells are kept activated/become activated. By using local immunotherapy, predominately tumor specific T cells residing in the tumour area, e.g. tumor, adjacent tissue and tumor draining lymph nodes, are activated. Local administration activates a lower number of T-cells but the T cells that are activated are more relevant for the purpose of tumour cell eradication. It is well known that T-cells, once fully activated can patrol the entire body, eradicating cells displaying a certain antigen, which in this case is shared only by the tumour cells. It is also well known that such activated T cells result in generation of memory T cells resulting in a long term memory that can protect from tumour relapse (Janeway's "Immunobiology" Seventh edition, Garland Science). The result of local CTLA-4 antagonist treatment is thus activation of tumour specific T-cells that can kill the treated tumour as well as distant metastases and also protect against relapse[9-11].

A local administration regime where an optimal dose is guided by $T_{reg}$ cells and $T_{eff}$ cells ratio provides an optimal anti-tumor effect while allowing administering a total dose that is much lower than the total dose given when treating the patients systemically, thereby reducing the risk for immune related adverse events (irAE). However, the concentration of the CTLA-4 antagonist in the tumour area can, using the local treatment method described herein, be higher than the concentration that can be given systemically. This dose is limited by the irAE that is induced. Thus, we can activate the tumour specific $T_{eff}$ cells residing in the tumour area more strongly compared to systemic administration of CTLA-4 antagonists.

Systemic anti-CTLA-4 treatment is dose limited by the toxic side effects (irAE). Systemic treatment with CTLA-4 antagonists are associated irAE, diarrhea, colitis, dermatitis, etc, which affects 60% of the treated patients[9, 13-17], and kills approximately 1%. This requires the patients to be closely observed for symptoms and may require hospitalization due to treatment of the side effects[9]. This is inconvenient for the patients, increase treatment costs and limit the efficacy of the treatment. This means that from an anti-tumor point of view, the maximal effective dose may be much higher, but systemic treatment is limited by the resulting systemic toxicity.

One promising approach to minimize the systemic side effects, while retaining or even improving the systemic anti-tumour effects is to use local administration of the CTLA-4 blocking agent. Local treatment will result in that a smaller number of T cells will be activated, but that the T-cells that are activated are predominantly T cells that have been exposed to, and therefore react to tumour cell antigens. This approach allows a dose that results in a higher local concentration yet still result in lower systemic toxicity.

The onset of the anti-tumour effects from systemic CTLA-4 treatment is delayed and standard response criteria such as Response Evaluation Criteria In Solid Tumors, RECIST, is not very efficient in predicting the outcome of this type of immunotherapy. RECIST criteria were developed to assess drugs that have immediate anti-tumour effects, and do not suit immunotherapeutic treatment protocols. Immediate response patterns are not uncommon; however, often there is a delayed response after initial progression. There is currently a lack of biomarkers that effectively predicts response to CTLA-4 treatment.

The invention described herein provides a method of determining optimal dose of a local CTLA-4 blocking agent, which is safe while generating highly effective anti-tumor response, in cancer immunotherapy.

Methods

Method for Designing a Personalized Maximally Effective Dose Regimen

The optimal effective dose may be individual and thus vary between patients, for example due to differences in genotype, pre-treatment conditions (e.g. prior non-related treatment), immune status, age as well as with tumour location, tumour size, tumour stage and other tumour-specific features. The optimal dose may also vary intra-individually, e.g. due to up/down regulation of target, treatment induced tolerance, immune status, age as well as with tumour location, tumour size and tumour stage.

Experimental Protocol

1. Blood samples and/or tumour biopsies and/or tumour draining lymph node biopsies are taken prior treatment from eligible patients to establish a base line $T_{reg}/T_{eff}$ ratio.
2. $T_{reg}/T_{eff}$ ratio is measured by flow cytometry analysis and or histochemistry.
   i. $T_{reg}$ cells are identified and quantified by markers such as, but not limited to CD25, CD4, CD3 and FoxP3.
   ii. $T_{eff}$ cells are identified and quantified by markers, such as, but not limited to CD3, CD4, CD8, IFNgamma, granzyme B, ICOS.
   iii. Immune related adverse events such as colitis, dermatitis etc are monitored using standard protocols.
3. The patients are treated intratumorally with immunomodulatory agent (preferably a CTLA-4-blocking agent alone or in a combination with a direct immune activator, such as a CD40 agonistic agent or IL2, or Il-15). The initial dose of the immunomodulatory agent will be defined from preclinical and/or clinical studies.
4. Blood samples and/or tumor biopsies and/or tumor draining lymph node biopsies are taken 4 weeks (conceivably from days to months) post treatment.
5. $T_{reg}/T_{eff}$ ratio is measured by flow cytometry analysis and or histochemistry as described in section 2.

6. If the $T_{reg}/T_{eff}$ ratio has decreased compared to the previous measurement and there are no severe Immune related adverse events, the dose (in mg/kg) of the immunomodulating agent is increased by 1.5 to 3 times (or more). If the $T_{reg}/T_{eff}$ has increased, the dose (in mg/kg) of the immunomodulating agent (preferably a CTLA-4-blocking agent alone or in a combination with a direct immune activator, such as a CD40 agonistic agent or IL2, or IL15) is decreased by 1.5 to 3 times (or more).

7. Step 5-7 is repeated every four weeks (conceivably from days to months).

8. The progress of the treatment is monitored by RECIST criteria, and/or Immune related response criteria (Wolchok et al 2009 *Clin Cancer Res;* 15(23):7412-742, and/or survival, and/or progression free survival etc. The treatment cycle is repeated until optimal treatment dose has been established or to complete response has been achieved. As the tumor treatment progress, the optimal dose may increase or decrease and the protocol will be continuously used to ensure that the dose level is optimized.

The treatment protocol/design described above aims at:
i. Identifying the optimal dose for an individual patient.
ii. Monitoring the treatment of an individual patient over time.

This is of particular importance for local treatment, since the optimal dose may vary over time (for reasons specified above).

Results and Discussion

Measurement of the ratio between effector T cells and regulatory T cells has several unexpected advantages in determining the optimal dose of local administration of a CTLA-4 antagonistic agent in treatment of cancer immunotherapy.

The optimal dose can be determined as the maximum dose of the CTLA-4 blocking agent that does not induce an increase in the number of local $T_{reg}$ cells in the patient.

Previous studies using systemic administration of CTLA-4 antagonists have demonstrated a normal dose response relationship, where increasing dose results in increasing anti-tumor effect but also increasing immune related adverse events, (FIG. 9). Unexpectedly, local CTLA-4-blockage therapy revealed an inverse dose-response relationship.

Local CTLA-4 blockade leads to high concentrations of anti-CTLA-4 agent at the tumor area with local $T_{reg}$ cells accumulation as a consequence. The increase in $T_{reg}$ cells after local treatment may counteract the positive effect of the $T_{eff}$ cells. Evidently, optimal dosing is crucial for effective therapy, and the data presented herein demonstrate that the ratio between T effector and T regulatory cells can be used for this purpose.

A local administration where an optimal dose is guided by $T_{reg}/T_{eff}$ cell ratio provides an optimal anti-tumour effect while allowing administration of a total dose that is much lower than the total dose given when treating the patients systemically, thereby reducing the risk for immune related adverse events (FIG. 10).

REFERENCES

Waldmann, T. A. Effective cancer therapy through immunomodulation. *Annu. Rev Med* 57, 65-81 (2006).
2. Stagg, J., Johnstone, R. W., & Smyth, M. J. From cancer immunosurveillance to cancer immunotherapy. *Immunol Rev.* 220:82-101, 82-101 (2007).
3. Melief, C. J. Cancer immunotherapy by dendritic cells. *Immunity.* 29, 372-383 (2008).
4. Melero, I., Hervas-Stubbs, S., Glennie, M., Pardoll, D. M., & Chen, L. Immunostimulatory monoclonal antibodies for cancer therapy. *Nat Rev Cancer.* 7, 95-106 (2007).
5. Waldmann, T. A. Effective cancer therapy through immunomodulation. *Annu, Rev Med.* 57:65-81, 65-81 (2006).
6. Khawli, L. A., Hu, P., & Epstein, A. L. Cytokine, chemokine, and co-stimulatory fusion proteins for the immunotherapy of solid tumors. Handb. Exp. Pharmacol. 291-328 (2008).
7. Berinstein, N. L. Enhancing cancer vaccines with immunomodulators. *Vaccine.* 25 Suppl 2:B72-88, B72-B88 (2007).
8. Mellor, A. L. & Munn, D. H. Creating immune privilege: active local suppression that benefits friends, but protects foes. *Nat Rev Immunol.* 8, 74-80 (2008).
9. Loskog, A. S., Fransson, M. E., & Totterman, T. T. AdCD40L gene therapy counteracts T regulatory cells and cures aggressive tumors in an orthotopic bladder cancer model. *Clin. Cancer Res.* 11, 8816-8821 (2005).
10. van Mierlo, G. J. et al. CD40 stimulation leads to effective therapy of CD40(-) tumors through induction of strong systemic cytotoxic T lymphocyte immunity. *Proc. Natl. Acad. Sci. U.S.A.* 99, 5561-5566 (2002).
11. von Euler, H. et al., Efficient adenovector CD40 ligand immunotherapy of canine malignant melanoma. *J Immunother* 31, 377-384 (2008).
12. Hodi, F. S. et al. Improved Survival with Ipilimumab in Patients with Metastatic Melanoma. *N. Engl. J Med* (2010).
13. Ribas, A. Overcoming immunologic tolerance to melanoma: targeting CTLA-4 with tremelimumab (CP-675, 206). *Oncologist.* 13 Suppl 4:10-5, 10-15 (2008).
14. Ribas, A. et al. Tremelimumab (CP-675,206), a cytotoxic T lymphocyte associated antigen 4 blocking monoclonal antibody in clinical development for patients with cancer. *Oncologist.* 12, 873-883 (2007).
15. O'Day, S. J., Hamid, O., & Urba, W. J. Targeting cytotoxic T-lymphocyte antigen-4 (CTLA-4): a novel strategy for the treatment of melanoma and other malignancies. *Cancer.* 110, 2614-2627 (2007).
16. Weber, J. S. et al. Phase I/II Study of Ipilimumab for Patients With Metastatic Melanoma. *J Clin Oncol.* (2008).
17. Weber, J. Review: anti-CTLA-4 antibody ipilimumab: case studies of clinical response and immune-related adverse events. *Oncologist.* 12, 864-872 (2007).

The invention claimed is:

1. A method for determining an optimal dose of an immunomodulatory agent for local treatment of a tumour in a patient comprising
(a) measuring the number of $T_{reg}$ cells in a sample of cells from the patient who has received local treatment of a tumour with an immunomodulatory agent at a test dose;
(b) repeating step (a) at one or more different test doses of the immunomodulatory agent to determine the maximum dose of the immunomodulatory agent that does not induce an increase in the number of $T_{reg}$ cells in the sample,
wherein the optimal dose is determined as the maximum dose of the immunomodulatory agent that does not induce an increase in the number of $T_{reg}$ cells.

2. The method of claim 1, wherein $T_{reg}$ cells are identified and quantified by the markers CD25, CD4, CD3, and FoxP3.

3. The method of claim 1, wherein the cell sample is a blood sample, a tumour biopsy, or a tumour draining lymph node biopsies.

4. The method according to claim 1 wherein the local treatment is by intratumoral injection, peritumoral injection, juxtatumoral injection, intralesional injection and/or injection into a tumour draining lymph node.

5. A method for determining an optimal dose of an immunomodulatory agent for local treatment of a tumour in a patient comprising
   (a) measuring the number of $T_{reg}$ cells in the sample of cells from a blood sample, a tumour biopsy, or a tumour draining lymph node biopsy from a patient who has received local treatment of a tumour with an immunomodulatory agent at a test dose;
   (b) repeating step (a) at one or more different test doses of the immunomodulatory agent to determine the maximum dose of the immunomodulatory agent that does not induce an increase in the number of $T_{reg}$ cells in the sample,
   wherein the optimal dose is determined as the maximum dose of the immunomodulatory agent that does not induce an increase in the number of $T_{reg}$ cells.

6. A method for determining an optimal dose of an immunomodulatory agent capable of inhibiting an activity of cytotoxic T lymphocyte antigen 4 (CTLA-4) for local treatment of a tumour in a patient comprising
   (a) measuring the number of $T_{reg}$ cells in the sample of cells from a patient who has received local treatment of a tumour with an immunomodulatory agent capable of inhibiting an activity of CTLA-4 at a test dose;
   (b) repeating step (a) at one or more different test doses of the immunomodulatory agent capable of inhibiting an activity of CTLA-4 to determine the maximum dose of the immunomodulatory agent capable of inhibiting an activity of CTLA-4 that does not induce an increase in the number of $T_{reg}$ cells in the sample,
   wherein the optimal dose is determined as a maximum dose of the immunomodulatory agent capable of inhibiting an activity of CTLA-4 that does not induce an increase in the number of $T_{reg}$ cells.

7. A method for determining an optimal dose of an immunomodulatory agent for the local treatment of a tumour in a patient comprising
   (a) locally administering to the patient a test dose of an immunomodulatory agent;
   (b) measuring the number of $T_{reg}$ cells in the sample of cells from a patient who has received local treatment of a tumour with an immunomodulatory agent at a test dose;
   (c) repeating steps (a) and (b) at one or more different test doses of the immunomodulatory agent to determine a maximum dose of the immunomodulatory agent that does not induce an increase in the number of $T_{reg}$ cells in the sample,
   wherein the optimal dose is determined as a maximum dose of the immunomodulatory agent that does not induce an increase in the number of $T_{reg}$ cells.

8. The method of claim 7, wherein $T_{reg}$ cells are identified and quantified by the markers CD25, CD4, CD3, and FoxP3.

9. The method of claim 7, wherein the cell sample is a blood sample, a tumour biopsy, or a tumour draining lymph node biopsies.

10. The method according to claim 7 wherein the local treatment is by intratumoral injection, peritumoral injection, juxtatumoral injection, intralesional injection and/or injection into a tumour draining lymph node.

11. A method of treatment of a tumour in a patient comprising the steps of
    (a) locally administering a test does of an immunomodulatory agent to a tumour of the patient;
    (b) measuring the number of $T_{reg}$ cells in a sample of cells from the patient;
    (c) measuring the number of effector cells in a sample of cells from the patient;
    (d) repeating steps (a)-(c) at one or more different test doses of the immunomodulatory agent;
    (e) determining the optimal dose of the immunomodulatory agent as the dose of the immunomodulatory agent that induces a maximal increase in the number of effector cells in the sample without inducing an increase in the number of $T_{reg}$ cells in the sample;
    (f) locally administering the optimal dose of the immunomodulatory agent to the tumour.

12. The method of claim 11, wherein $T_{reg}$ cells are identified and quantified by the markers CD25, CD4, CD3, and FoxP3.

13. The method of claim 11, wherein the cell sample is a blood sample, a tumour biopsy, or a tumour draining lymph node biopsies.

14. The method according to claim 11 wherein the local treatment is by intratumoral injection, peritumoral injection, juxtatumoral injection, intralesional injection and/or injection into a tumour draining lymph node.

* * * * *